(12) United States Patent
Hansen et al.

(10) Patent No.: US 11,717,433 B2
(45) Date of Patent: Aug. 8, 2023

(54) MEDICAL APPLIANCE WITH ANGULAR LEAKAGE DETECTION

(71) Applicant: Coloplast A/S, Humlebaek (DK)

(72) Inventors: Jais Ask Hansen, Jaegerspris (DK); Lars Erup Larsen, Maaloev (EC); Niels Hvid, Vedbaek (DK); Finn Speiermann, Virum (DK); Klaus Thoegersen, Charlottenlund (DK)

(73) Assignee: Coloplast A/S, Humlebaek (DK)

( * ) Notice: Subject to any disclaimer, the term of this patent is extended or adjusted under 35 U.S.C. 154(b) by 81 days.

(21) Appl. No.: 16/955,050

(22) PCT Filed: Dec. 20, 2018

(86) PCT No.: PCT/DK2018/050393
§ 371 (c)(1),
(2) Date: Jun. 18, 2020

(87) PCT Pub. No.: WO2019/120437
PCT Pub. Date: Jun. 27, 2019

(65) Prior Publication Data
US 2021/0369488 A1 Dec. 2, 2021

(30) Foreign Application Priority Data

Dec. 22, 2017 (DK) .......................... PA 2017 70979
Dec. 22, 2017 (DK) .......................... PA 2017 70994
Feb. 5, 2018 (DK) .......................... PA 2018 70070

(51) Int. Cl.
*A61F 5/443* (2006.01)
*A61F 5/44* (2006.01)
*A61B 5/00* (2006.01)

(52) U.S. Cl.
CPC .......... *A61F 5/4404* (2013.01); *A61B 5/0002* (2013.01); *A61B 5/4851* (2013.01); *A61F 5/443* (2013.01); *A61B 2560/02* (2013.01)

(58) Field of Classification Search
CPC ...... A61F 5/4404; A61F 5/443; A61B 5/0002; A61B 5/4851; A61B 2560/02
See application file for complete search history.

(56) References Cited

U.S. PATENT DOCUMENTS 2,054,535 A 9/1936 Diack
2,327,514 A * 8/1943 Fenwick ................. A61F 5/445
604/338

(Continued)

FOREIGN PATENT DOCUMENTS

CN 203786580 U 8/2014
CN 104902399 A 9/2015
(Continued)

*Primary Examiner* — Guy K Townsend
(74) *Attorney, Agent, or Firm* — Coloplast Corp., Coloplast A/S; Nick Baumann

(57) ABSTRACT

A base plate and/or a sensor assembly part for an ostomy appliance and related method is disclosed, the base plate and/or the sensor assembly part comprising: a first adhesive layer with a proximal side configured for attachment of the base plate and/or the sensor assembly part to the skin surface of a user, the first adhesive layer having a stomal opening with a center point; and a plurality of electrodes including a first leakage electrode, a second leakage electrode, and a third leakage electrode, wherein the plurality of electrodes is configured to detect presence of fluid on the proximal side of the first adhesive layer in a primary sensing zone and a secondary sensing zone, the primary sensing zone arranged in a primary angle space from the center point of the first adhesive layer and the secondary sensing zone arranged in a secondary angle space from the center point of the first adhesive layer.

17 Claims, 15 Drawing Sheets

(56) References Cited

U.S. PATENT DOCUMENTS

| | | | |
|---|---|---|---|
| 2,542,233 A * | 2/1951 | Carroll | A61F 5/445 604/337 |
| 2,544,579 A * | 3/1951 | Ardner | A61F 5/445 604/337 |
| 3,214,502 A | 10/1965 | Schaar | |
| 3,832,510 A | 8/1974 | Pfau et al. | |
| 3,915,171 A | 10/1975 | Shermeta | |
| 3,941,133 A | 3/1976 | Chen | |
| 4,231,369 A | 11/1980 | Sorensen et al. | |
| 4,372,308 A | 2/1983 | Steer et al. | |
| 4,449,970 A | 5/1984 | Bevan et al. | |
| 4,668,227 A | 5/1987 | Kay | |
| 4,754,264 A | 6/1988 | Okada et al. | |
| 4,775,374 A | 10/1988 | Cilento et al. | |
| 4,834,731 A | 5/1989 | Nowak et al. | |
| 4,973,323 A | 11/1990 | Kaczmarek et al. | |
| 4,982,742 A | 1/1991 | Claude | |
| 5,013,307 A | 5/1991 | Broida | |
| 5,016,645 A * | 5/1991 | Williams | A61N 1/0587 607/129 |
| 5,051,259 A | 9/1991 | Olsen et al. | |
| 5,074,851 A | 12/1991 | Plass et al. | |
| 5,111,812 A | 5/1992 | Swanson et al. | |
| 5,167,650 A | 12/1992 | Johnsen et al. | |
| 5,197,895 A | 3/1993 | Stupecky | |
| 5,237,995 A | 8/1993 | Cano | |
| 5,318,543 A | 6/1994 | Ross et al. | |
| 5,358,488 A | 10/1994 | Suriyapa | |
| 5,486,158 A | 1/1996 | Samuelsen | |
| 5,570,082 A | 10/1996 | Mahgerefteh et al. | |
| 5,593,397 A | 1/1997 | La Gro | |
| 5,672,163 A * | 9/1997 | Ferreira | A61F 5/441 604/333 |
| 5,677,221 A | 10/1997 | Tseng | |
| 5,704,905 A | 1/1998 | Jensen et al. | |
| 5,790,036 A | 8/1998 | Fisher et al. | |
| 5,800,415 A | 9/1998 | Olsen | |
| 5,816,252 A | 10/1998 | Faries, Jr. et al. | |
| 5,834,009 A | 11/1998 | Sawers et al. | |
| 5,879,292 A | 3/1999 | Sternberg et al. | |
| 6,015,399 A | 1/2000 | Mracna et al. | |
| 6,025,725 A | 2/2000 | Gershenfeld et al. | |
| 6,057,689 A | 5/2000 | Saadat | |
| 6,103,033 A | 8/2000 | Say et al. | |
| 6,135,986 A * | 10/2000 | Leisner | A61F 5/441 604/324 |
| 6,165,005 A | 12/2000 | Mills et al. | |
| 6,171,289 B1 * | 1/2001 | Millot | A61F 5/443 604/336 |
| 6,206,864 B1 | 3/2001 | Kavanagh et al. | |
| 6,246,330 B1 | 6/2001 | Nielsen | |
| 6,297,422 B1 | 10/2001 | Hansen et al. | |
| 6,407,308 B1 | 6/2002 | Roe et al. | |
| 6,433,244 B1 | 8/2002 | Roe et al. | |
| 6,482,491 B1 | 11/2002 | Samuelsen et al. | |
| 6,485,476 B1 | 11/2002 | von Dyck et al. | |
| 6,520,943 B1 | 2/2003 | Wagner | |
| 6,524,675 B1 | 2/2003 | Mikami et al. | |
| 6,659,989 B1 | 12/2003 | Otto | |
| 6,764,474 B2 | 7/2004 | Nielsen et al. | |
| 7,049,478 B1 | 5/2006 | Smith | |
| 7,066,919 B1 | 6/2006 | Sauerland et al. | |
| 7,150,728 B2 | 12/2006 | Hansen et al. | |
| 7,166,091 B1 * | 1/2007 | Zeltner | A61F 5/445 604/338 |
| 7,199,501 B2 | 4/2007 | Pei et al. | |
| 7,214,217 B2 | 5/2007 | Pedersen et al. | |
| 7,221,279 B2 | 5/2007 | Nielsen | |
| 7,326,190 B2 * | 2/2008 | Botten | A61F 5/441 604/332 |
| 7,341,578 B2 * | 3/2008 | Bulow | A61F 5/441 604/338 |
| 7,347,844 B2 | 3/2008 | Cline et al. | |
| 7,367,965 B2 * | 5/2008 | Poulsen | A61F 5/441 604/324 |
| 7,422,578 B2 | 9/2008 | Shan et al. | |
| 7,559,922 B2 * | 7/2009 | Botten | A61F 5/441 604/332 |
| 7,625,362 B2 * | 12/2009 | Boehringer | A61M 1/74 604/304 |
| 7,641,612 B1 | 1/2010 | McCall | |
| 7,670,289 B1 | 3/2010 | McCall | |
| 7,943,812 B2 | 5/2011 | Stroebeck et al. | |
| 7,981,098 B2 * | 7/2011 | Boehringer | A61M 1/74 604/319 |
| 3,061,360 A1 | 11/2011 | Locke et al. | |
| 8,277,427 B2 | 10/2012 | Edvardsen et al. | |
| 8,319,003 B2 | 11/2012 | Olsen et al. | |
| 8,398,575 B1 | 3/2013 | McCall | |
| 8,398,603 B2 * | 3/2013 | Thirstrup | A61B 5/746 602/41 |
| 8,399,732 B2 | 3/2013 | Oelund et al. | |
| 8,409,158 B2 * | 4/2013 | Edvardsen | A61F 5/443 604/335 |
| 8,449,471 B2 | 5/2013 | Tran | |
| 8,474,338 B2 | 7/2013 | Gelman et al. | |
| 8,500,718 B2 | 8/2013 | Locke et al. | |
| 8,632,492 B2 | 1/2014 | DeLegge | |
| 8,680,991 B2 | 3/2014 | Tran | |
| 8,684,982 B2 * | 4/2014 | Nguyen-DeMary | A61F 5/441 604/327 |
| 8,740,865 B2 | 6/2014 | Krystek et al. | |
| 8,795,257 B2 | 8/2014 | Coulthard et al. | |
| D712,545 S | 9/2014 | Igwebuike et al. | |
| 8,821,464 B2 | 9/2014 | Manuka et al. | |
| 8,975,465 B2 | 3/2015 | Hong et al. | |
| 8,979,813 B2 | 3/2015 | Uveborn | |
| 9,046,085 B2 | 6/2015 | Schoess et al. | |
| 9,066,812 B2 * | 6/2015 | Edvardsen | A61F 5/443 |
| 9,216,104 B2 * | 12/2015 | Thirstrup | A61F 5/4404 |
| 9,308,332 B2 * | 4/2016 | Heppe | A61M 1/3656 |
| 9,322,797 B1 * | 4/2016 | Lastinger | G01N 27/12 |
| 9,629,779 B2 | 4/2017 | Grum-Schwensen et al. | |
| 9,629,964 B2 * | 4/2017 | Wuepper | A61B 5/02042 |
| 9,693,908 B2 | 7/2017 | Eriksson et al. | |
| 9,770,359 B2 | 9/2017 | Edvardsen et al. | |
| 9,788,991 B2 | 10/2017 | Bird | |
| 9,867,934 B2 | 1/2018 | Heppe | |
| 9,928,341 B2 * | 3/2018 | Angelides | G16H 40/67 |
| 10,016,298 B2 * | 7/2018 | Thirstrup | A61F 13/42 |
| D826,740 S | 8/2018 | Stevens et al. | |
| 10,500,084 B2 * | 12/2019 | Hansen | A61B 5/7475 |
| 10,531,977 B2 * | 1/2020 | Schoess | A61F 5/445 |
| 10,646,370 B2 * | 5/2020 | Keleny | A61F 5/441 |
| 10,792,184 B2 | 10/2020 | Hvid et al. | |
| 10,799,385 B2 * | 10/2020 | Hansen | A61F 5/445 |
| 10,849,781 B2 * | 12/2020 | Hansen | A61B 5/6833 |
| 10,874,541 B2 * | 12/2020 | Seres | A61B 5/002 |
| 10,987,243 B2 * | 4/2021 | Thirstrup | A61B 5/746 |
| 11,096,818 B2 * | 8/2021 | Thirstrup | A61F 13/02 |
| 11,135,084 B2 * | 10/2021 | Seres | A61B 5/14539 |
| 11,406,525 B2 * | 8/2022 | Seres | A61B 5/14539 |
| 11,471,318 B2 * | 10/2022 | Hansen | A61F 5/448 |
| 11,491,042 B2 * | 11/2022 | Seres | A61B 5/14539 |
| 11,534,323 B2 * | 12/2022 | Hansen | A61F 2/64 |
| 11,540,937 B2 | 1/2023 | Hansen et al. | |
| 11,547,595 B2 * | 1/2023 | Hansen | A61B 5/6833 |
| 11,547,596 B2 * | 1/2023 | Hansen | A61F 5/4404 |
| 11,559,423 B2 * | 1/2023 | Speiermann | A61B 5/150809 |
| 11,559,426 B2 * | 1/2023 | Sletten | A61F 5/44 |
| 2002/0019615 A1 | 2/2002 | Roe et al. | |
| 2003/0132763 A1 | 7/2003 | Ellenz | |
| 2003/0169032 A1 | 9/2003 | Minchole et al. | |
| 2004/0006320 A1 | 1/2004 | Buglino et al. | |
| 2004/0030305 A1 | 2/2004 | Sakamoto | |
| 2004/0036484 A1 * | 2/2004 | Tamai | G01N 27/225 324/663 |
| 2004/0049145 A1 | 3/2004 | Flick | |
| 2004/0068244 A1 | 4/2004 | Salone et al. | |
| 2004/0078219 A1 | 4/2004 | Kaylor et al. | |
| 2004/0100376 A1 | 5/2004 | Lye et al. | |

(56) References Cited

U.S. PATENT DOCUMENTS

| | | |
|---|---|---|
| 2004/0106908 A1 | 6/2004 | Leise, Jr. et al. |
| 2004/0111072 A1 | 6/2004 | McKissick |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1* | 3/2005 | Bulow .................... A61F 5/441 604/332 |
| 2005/0085779 A1* | 4/2005 | Poulsen ................ A61F 5/441 604/332 |
| 2005/0101841 A9 | 5/2005 | Kaylor et al. |
| 2005/0240163 A1 | 10/2005 | Andersen |
| 2005/0261645 A1* | 11/2005 | Conrad .................... A61F 5/445 604/332 |
| 2006/0015081 A1 | 1/2006 | Suzuki et al. |
| 2006/0025727 A1* | 2/2006 | Boehringer ............ A61M 1/966 604/313 |
| 2006/0052752 A1 | 3/2006 | McMichael |
| 2006/0194324 A1 | 8/2006 | Faries et al. |
| 2006/0271002 A1* | 11/2006 | Botten .................... A61F 5/441 604/339 |
| 2007/0010256 A1 | 1/2007 | Klabunde et al. |
| 2007/0035405 A1 | 2/2007 | Wada et al. |
| 2007/0135782 A1 | 6/2007 | Bager et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow, Jr. et al. |
| 2008/0091154 A1* | 4/2008 | Botten .................... A61F 5/441 96/155 |
| 2008/0096726 A1 | 4/2008 | Riley et al. |
| 2008/0097360 A1 | 4/2008 | Andersen et al. |
| 2008/0140057 A1 | 6/2008 | Wood et al. |
| 2008/0234641 A1 | 9/2008 | Locke et al. |
| 2008/0275327 A1* | 11/2008 | Faarbaek ............ A61B 5/68335 600/382 |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0012501 A1* | 1/2009 | Boehringer ............ A61M 1/966 604/543 |
| 2009/0118600 A1 | 5/2009 | Ortiz et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0216169 A1 | 8/2009 | Hansen et al. |
| 2009/0227969 A1 | 9/2009 | Jaeb et al. |
| 2009/0247970 A1* | 10/2009 | Keleny ............. B01D 46/0036 156/247 |
| 2010/0010460 A1* | 1/2010 | Butler .................... A61F 5/441 604/333 |
| 2010/0030167 A1* | 2/2010 | Thirstrup .............. A61F 5/4404 340/657 |
| 2010/0036206 A1 | 2/2010 | Lorio |
| 2010/0072271 A1 | 3/2010 | Thorstensson |
| 2010/0076275 A1 | 3/2010 | Chu et al. |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2012/0013130 A1 | 1/2012 | Jung |
| 2012/0143154 A1* | 6/2012 | Edvardsen ............ A61F 5/4404 604/336 |
| 2012/0143155 A1* | 6/2012 | Edvardsen ............ A61F 5/443 604/318 |
| 2012/0253224 A1 | 10/2012 | Mir et al. |
| 2012/0258302 A1 | 10/2012 | Hunt et al. |
| 2012/0259230 A1 | 10/2012 | Riley |
| 2012/0283678 A1* | 11/2012 | Nguyen-DeMary .... A61F 5/445 604/338 |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1* | 3/2013 | Schertiger ............... A61F 5/445 604/335 |
| 2013/0102979 A1 | 4/2013 | Coulthard et al. |
| 2013/0138065 A1 | 5/2013 | Buus |
| 2013/0150769 A1* | 6/2013 | Heppe ................. A61M 1/3656 604/6.16 |
| 2013/0165862 A1 | 6/2013 | Griffith et al. |
| 2013/0192604 A1* | 8/2013 | Persson ............... A61M 16/047 128/207.16 |
| 2013/0231620 A1* | 9/2013 | Thirstrup ................ A61F 5/445 604/344 |
| 2013/0261575 A1 | 10/2013 | Kiyoshi |
| 2013/0267790 A1 | 10/2013 | Pfuetzner et al. |
| 2013/0303867 A1 | 11/2013 | Elfstrom et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0236335 A1 | 8/2014 | Lewis et al. |
| 2014/0275854 A1 | 9/2014 | Venkatraman et al. |
| 2014/0276501 A1* | 9/2014 | Cisko ..................... A61F 5/443 604/355 |
| 2014/0288381 A1* | 9/2014 | Faarbaek ............ A61B 5/0002 600/300 |
| 2014/0303574 A1 | 10/2014 | Knutson |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1* | 9/2015 | Thirstrup .......... A61F 13/00051 156/278 |
| 2015/0257923 A1* | 9/2015 | Thirstrup ............... A61F 13/42 604/318 |
| 2015/0342777 A1 | 12/2015 | Seres et al. |
| 2015/0351690 A1 | 12/2015 | Toth et al. |
| 2015/0374896 A1 | 12/2015 | Du et al. |
| 2016/0015570 A1 | 1/2016 | Heinecke et al. |
| 2016/0084869 A1 | 3/2016 | Yuen et al. |
| 2016/0158056 A1* | 6/2016 | Davis ..................... A61F 5/443 29/872 |
| 2016/0158969 A1 | 6/2016 | McLane et al. |
| 2016/0166438 A1* | 6/2016 | Rovaniemi ............ A61F 13/42 493/320 |
| 2016/0218555 A1 | 7/2016 | Slaby et al. |
| 2016/0235581 A1* | 8/2016 | Keleny .................... A61F 5/441 |
| 2016/0278990 A1 | 9/2016 | Chen |
| 2016/0284084 A1 | 9/2016 | Gurcan et al. |
| 2016/0305776 A1 | 10/2016 | Martensson et al. |
| 2016/0310140 A1 | 10/2016 | Belson et al. |
| 2016/0310329 A1 | 10/2016 | Patel et al. |
| 2016/0317728 A1 | 11/2016 | Lewis et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0079530 A1 | 3/2017 | DiMaio et al. |
| 2017/0079576 A1 | 3/2017 | Stroebech et al. |
| 2017/0140103 A1* | 5/2017 | Angelides ............ A61F 5/4404 |
| 2017/0156920 A1 | 6/2017 | Hunt et al. |
| 2017/0262986 A1 | 9/2017 | Xiong et al. |
| 2017/0319073 A1 | 11/2017 | DiMaio et al. |
| 2017/0340474 A1* | 11/2017 | Thirstrup ............... A61B 5/746 |
| 2017/0348137 A1 | 12/2017 | Hvid et al. |
| 2017/0360592 A1 | 12/2017 | Carrubba |
| 2018/0021164 A1 | 1/2018 | Fenton |
| 2018/0021165 A1 | 1/2018 | Fenton |
| 2018/0049667 A1 | 2/2018 | Heppe |
| 2018/0055359 A1 | 3/2018 | Shamim et al. |
| 2018/0078163 A1 | 3/2018 | Welch |
| 2018/0109852 A1 | 4/2018 | Mandapaka et al. |
| 2018/0171183 A1 | 6/2018 | Sakurai et al. |
| 2018/0177626 A1 | 6/2018 | Israelson |
| 2018/0250156 A1 | 9/2018 | Lam |
| 2018/0344533 A1* | 12/2018 | Rovaniemi ......... A61F 13/0243 |

(56) References Cited

U.S. PATENT DOCUMENTS

| | | | |
|---|---|---|---|
| 2019/0099552 A1 | 4/2019 | Zhang et al. | |
| 2019/0133810 A1* | 5/2019 | Seres | A61F 5/448 |
| 2019/0133811 A1* | 5/2019 | Seres | A61B 5/6802 |
| 2019/0133812 A1* | 5/2019 | Seres | A61B 5/002 |
| 2019/0142623 A1* | 5/2019 | Schoess | A61F 5/4404 604/336 |
| 2019/0175386 A1* | 6/2019 | Monty | A61F 5/445 |
| 2019/0192066 A1 | 6/2019 | Schoess et al. | |
| 2019/0192332 A1* | 6/2019 | Hansen | A61B 5/7405 |
| 2019/0192333 A1* | 6/2019 | Hansen | A61F 5/44 |
| 2019/0192334 A1* | 6/2019 | Hansen | G01M 3/40 |
| 2019/0240059 A1* | 8/2019 | Seres | G16H 40/67 |
| 2019/0247050 A1* | 8/2019 | Goldsmith | A61F 2/82 |
| 2019/0374163 A1* | 12/2019 | Faarbaek | A61B 5/6833 |
| 2019/0374372 A1* | 12/2019 | Seres | A61B 5/6802 |
| 2020/0100931 A1* | 4/2020 | Schoess | A61F 5/443 |
| 2020/0188161 A1* | 6/2020 | Seres | G01K 13/00 |
| 2020/0246174 A1* | 8/2020 | Hansen | A61F 5/444 |
| 2020/0246175 A1* | 8/2020 | Hansen | G01M 3/16 |
| 2020/0246176 A1* | 8/2020 | Hansen | A61F 5/445 |
| 2020/0246177 A1* | 8/2020 | Hansen | A61F 5/443 |
| 2020/0276063 A1 | 9/2020 | Munoz Herencia | |
| 2020/0306074 A1* | 10/2020 | Speiermann | A61B 5/150809 |
| 2020/0330258 A1* | 10/2020 | Hansen | A61F 13/15577 |
| 2020/0330260 A1* | 10/2020 | Hansen | A61F 5/445 |
| 2020/0337880 A1* | 10/2020 | Hansen | A61F 5/443 |
| 2020/0337881 A1* | 10/2020 | Hansen | A61F 5/443 |
| 2020/0337882 A1 | 10/2020 | Hansen et al. | |
| 2020/0337883 A1* | 10/2020 | Hansen | A61F 5/443 |
| 2020/0375499 A1 | 12/2020 | Hansen et al. | |
| 2020/0375782 A1* | 12/2020 | Hansen | G01M 3/40 |
| 2020/0375783 A1* | 12/2020 | Hansen | A61B 5/7475 |
| 2020/0375784 A1* | 12/2020 | Hansen | A61F 5/445 |
| 2020/0375785 A1* | 12/2020 | Hansen | G16H 30/40 |
| 2020/0375786 A1* | 12/2020 | Hansen | A61F 5/443 |
| 2020/0383637 A1* | 12/2020 | Hansen | A61B 90/96 |
| 2020/0383818 A1* | 12/2020 | Hansen | A61F 5/443 |
| 2020/0383819 A1* | 12/2020 | Sletten | A61F 5/443 |
| 2020/0383820 A1* | 12/2020 | Hansen | A61F 5/445 |
| 2020/0383821 A1* | 12/2020 | Hansen | A61F 5/4404 |
| 2020/0390587 A1* | 12/2020 | Svanegaard | A61F 5/4404 |
| 2020/0390588 A1* | 12/2020 | Hansen | A61F 5/4404 |
| 2020/0390589 A1* | 12/2020 | Hansen | A61F 5/443 |
| 2020/0395120 A1* | 12/2020 | Svanegaard | A61B 5/4255 |
| 2020/0395610 A1 | 12/2020 | Ono et al. | |
| 2020/0405228 A1* | 12/2020 | Svanegaard | A61B 5/002 |
| 2020/0405229 A1* | 12/2020 | Svanegaard | A61B 5/6833 |
| 2020/0405230 A1* | 12/2020 | Svanegaard | A61B 5/6813 |
| 2021/0000414 A1* | 1/2021 | Svanegaard | A61B 5/4851 |
| 2021/0000633 A1* | 1/2021 | Hansen | A61B 5/4851 |
| 2021/0000634 A1* | 1/2021 | Svanegaard | A61B 5/0022 |
| 2021/0000635 A1* | 1/2021 | Hansen | A61F 5/44 |
| 2021/0000636 A1* | 1/2021 | Hansen | A61F 5/443 |
| 2021/0007663 A1* | 1/2021 | Svanegaard | A61B 5/742 |
| 2021/0007881 A1* | 1/2021 | Svanegaard | G01C 19/00 |
| 2021/0015653 A1* | 1/2021 | Hansen | A61B 5/4851 |
| 2021/0015654 A1* | 1/2021 | Hansen | A61B 5/6833 |
| 2021/0022683 A1* | 1/2021 | Faarbaek | A61B 5/259 |
| 2021/0038424 A1* | 2/2021 | Svanegaard | A61B 5/6843 |
| 2021/0059603 A1* | 3/2021 | Svanegaard | A61F 5/443 |
| 2021/0085511 A1* | 3/2021 | Hansen | A61B 5/6833 |
| 2021/0085512 A1* | 3/2021 | Hansen | A61F 5/4404 |
| 2021/0100533 A1* | 4/2021 | Seres | A61B 5/42 |
| 2021/0128364 A1 | 5/2021 | Cole et al. | |
| 2021/0177642 A1* | 6/2021 | Andersen | A61F 5/443 |
| 2021/0212855 A1* | 7/2021 | Hansen | A61B 5/6811 |
| 2021/0228194 A1 | 7/2021 | Mayberg | |
| 2021/0338471 A1* | 11/2021 | Nolan | A61F 5/4404 |
| 2021/0361464 A1* | 11/2021 | Larsen | A61F 5/443 |
| 2021/0361465 A1* | 11/2021 | Hansen | A61F 5/445 |
| 2021/0361466 A1 | 11/2021 | Hansen et al. | |
| 2021/0361467 A1* | 11/2021 | Hansen | A61B 5/1118 |
| 2021/0369197 A1* | 12/2021 | Hansen | A61B 5/7405 |
| 2021/0369488 A1* | 12/2021 | Hansen | A61F 5/445 |
| 2021/0369489 A1* | 12/2021 | Hansen | B29C 65/48 |
| 2021/0369490 A1* | 12/2021 | Hansen | A61F 5/4404 |
| 2022/0000652 A1* | 1/2022 | Thirstrup | A61F 5/443 |
| 2022/0031495 A1* | 2/2022 | Seres | A61B 5/01 |
| 2022/0079802 A1 | 3/2022 | Hansen | |
| 2022/0079803 A1 | 3/2022 | Windeballe et al. | |
| 2022/0087851 A1 | 3/2022 | Stroebech | |
| 2022/0117771 A1 | 4/2022 | Feam et al. | |
| 2022/0142807 A1 | 5/2022 | Tofte | |
| 2022/0192860 A1 | 6/2022 | Hansen et al. | |
| 2022/0241104 A1 | 8/2022 | Knoedler | |
| 2022/0241105 A1 | 8/2022 | Hansen et al. | |
| 2022/0265458 A1 | 8/2022 | Carlsson et al. | |
| 2022/0378602 A1* | 12/2022 | Hansen | A61F 5/448 |

FOREIGN PATENT DOCUMENTS

| | | |
|---|---|---|
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 69722993 | 7/2003 |
| DE | 102011014321 A1 | 9/2012 |
| DE | 102011076219 A1 | 11/2012 |
| EP | 0168967 A1 | 1/1986 |
| EP | 0373782 B1 | 10/1994 |
| EP | 0416397 B1 | 5/1995 |
| EP | 0896211 A2 | 2/1999 |
| EP | 0800804 B1 | 6/2003 |
| EP | 1188157 B1 | 12/2005 |
| EP | 2108345 A1 | 10/2009 |
| EP | 1275357 B1 | 3/2011 |
| EP | 2000083 B1 | 8/2012 |
| EP | 2601915 A1 | 6/2013 |
| EP | 2738960 A1 | 6/2014 |
| EP | 2489561 B1 | 8/2014 |
| EP | 2453851 B1 | 10/2014 |
| EP | 2654646 B1 | 7/2016 |
| EP | 3226946 A1 | 10/2017 |
| EP | 3213727 B1 | 12/2019 |
| EP | 3064179 B1 | 9/2021 |
| GB | 2219679 A | 12/1989 |
| GB | 2308306 B | 9/1999 |
| GB | 2343628 A1 | 5/2000 |
| GB | 2465742 B | 7/2012 |
| GB | 2486968 B | 2/2015 |
| GB | 2542093 A | 3/2017 |
| GB | 2561193 B | 9/2020 |
| JP | H0474882 A | 3/1992 |
| JP | H06152077 A | 5/1994 |
| JP | H0910184 A | 1/1997 |
| JP | H11128352 A | 5/1999 |
| JP | 2000093448 A | 4/2000 |
| JP | 2001087299 A | 4/2001 |
| JP | 2002055074 A | 2/2002 |
| JP | 2002224093 A | 8/2002 |
| JP | 2005323981 A | 11/2005 |
| JP | 2007319561 A | 12/2007 |
| JP | 2009519751 A | 5/2009 |
| JP | 2014033745 A | 2/2014 |
| JP | 2014054368 A | 3/2014 |
| JP | 2014507182 A | 3/2014 |
| KR | 101056989 B1 | 8/2011 |
| KR | 20120003987 A | 1/2012 |
| KR | 200485138 Y1 | 12/2017 |
| NL | 1001019 C2 | 2/1997 |
| NL | 1003904 C2 | 3/1998 |
| TW | 201201783 A | 1/2012 |
| WO | 1994015562 A1 | 7/1994 |
| WO | 1997010012 A1 | 3/1997 |
| WO | 9933037 A1 | 7/1999 |
| WO | 1999036017 A1 | 7/1999 |
| WO | 0079497 A1 | 12/2000 |
| WO | 2001013830 A1 | 3/2001 |
| WO | 2001050996 A1 | 7/2001 |

(56) References Cited

FOREIGN PATENT DOCUMENTS

| | | |
|---|---|---|
| WO | 2002052302 A2 | 7/2002 |
| WO | 2002099765 A1 | 12/2002 |
| WO | 2005038693 A1 | 4/2005 |
| WO | 2005082271 A2 | 9/2005 |
| WO | 2006008866 A1 | 1/2006 |
| WO | 2006094513 A2 | 9/2006 |
| WO | 2007000168 A1 | 1/2007 |
| WO | 2007059774 A2 | 5/2007 |
| WO | 2007070266 A1 | 6/2007 |
| WO | 2007098762 A1 | 9/2007 |
| WO | 2007133555 A2 | 11/2007 |
| WO | 2008057884 A2 | 5/2008 |
| WO | 2009006900 A1 | 1/2009 |
| WO | 2009052496 A1 | 4/2009 |
| WO | 2009107011 A1 | 9/2009 |
| WO | 2009112912 A2 | 9/2009 |
| WO | 2011003421 A1 | 1/2011 |
| WO | 2011004165 A1 | 1/2011 |
| WO | 2011061540 A1 | 5/2011 |
| WO | 2011105701 A2 | 9/2011 |
| WO | 2011123018 A1 | 10/2011 |
| WO | 2011139499 A1 | 11/2011 |
| WO | 2011161254 A2 | 12/2011 |
| WO | 2012068386 A1 | 5/2012 |
| WO | 2012076022 A2 | 6/2012 |
| WO | 2012084987 A2 | 6/2012 |
| WO | 2013013197 A1 | 1/2013 |
| WO | 2014004207 A1 | 1/2014 |
| WO | 2014086369 A1 | 6/2014 |
| WO | 2015007284 A1 | 1/2015 |
| WO | 2015014774 A1 | 2/2015 |
| WO | 2015084462 A1 | 6/2015 |
| WO | 2015094064 A1 | 6/2015 |
| WO | 2015187366 A1 | 12/2015 |
| WO | 2016132738 A1 | 8/2016 |
| WO | 2016166731 A1 | 10/2016 |
| WO | 2016192738 A1 | 12/2016 |
| WO | 2017023794 A1 | 2/2017 |
| WO | 2017062042 A1 | 4/2017 |
| WO | 2017067558 A1 | 4/2017 |
| WO | 2017067560 A1 | 4/2017 |
| WO | 2017074505 A1 | 5/2017 |
| WO | 2017088153 A1 | 6/2017 |
| WO | 2017136696 A1 | 8/2017 |
| WO | 2017190752 A1 | 11/2017 |
| WO | 2018028756 A1 | 2/2018 |
| WO | 2019094635 A1 | 5/2019 |
| WO | 2019120432 A1 | 6/2019 |
| WO | 2019161859 A1 | 8/2019 |
| WO | 2019161860 A1 | 8/2019 |
| WO | 2019161863 A1 | 8/2019 |
| WO | 2019174693 A1 | 9/2019 |
| WO | 2019174695 A1 | 9/2019 |
| WO | 2019213623 A1 | 11/2019 |
| WO | 2020035121 A1 | 2/2020 |

\* cited by examiner

MEDICAL APPLIANCE WITH ANGULAR LEAKAGE DETECTION

The present disclosure relates to a base plate and/or a sensor assembly part for an ostomy appliance. An ostomy system, and devices of the ostomy system are also disclosed. The ostomy appliance system comprises an ostomy appliance and a monitor device. In particular, the present disclosure relates to a base plate and/or a sensor assembly part and an ostomy appliance enabling or facilitating leakage classification and/or detection for an ostomy appliance and/or monitoring the operation of an ostomy appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
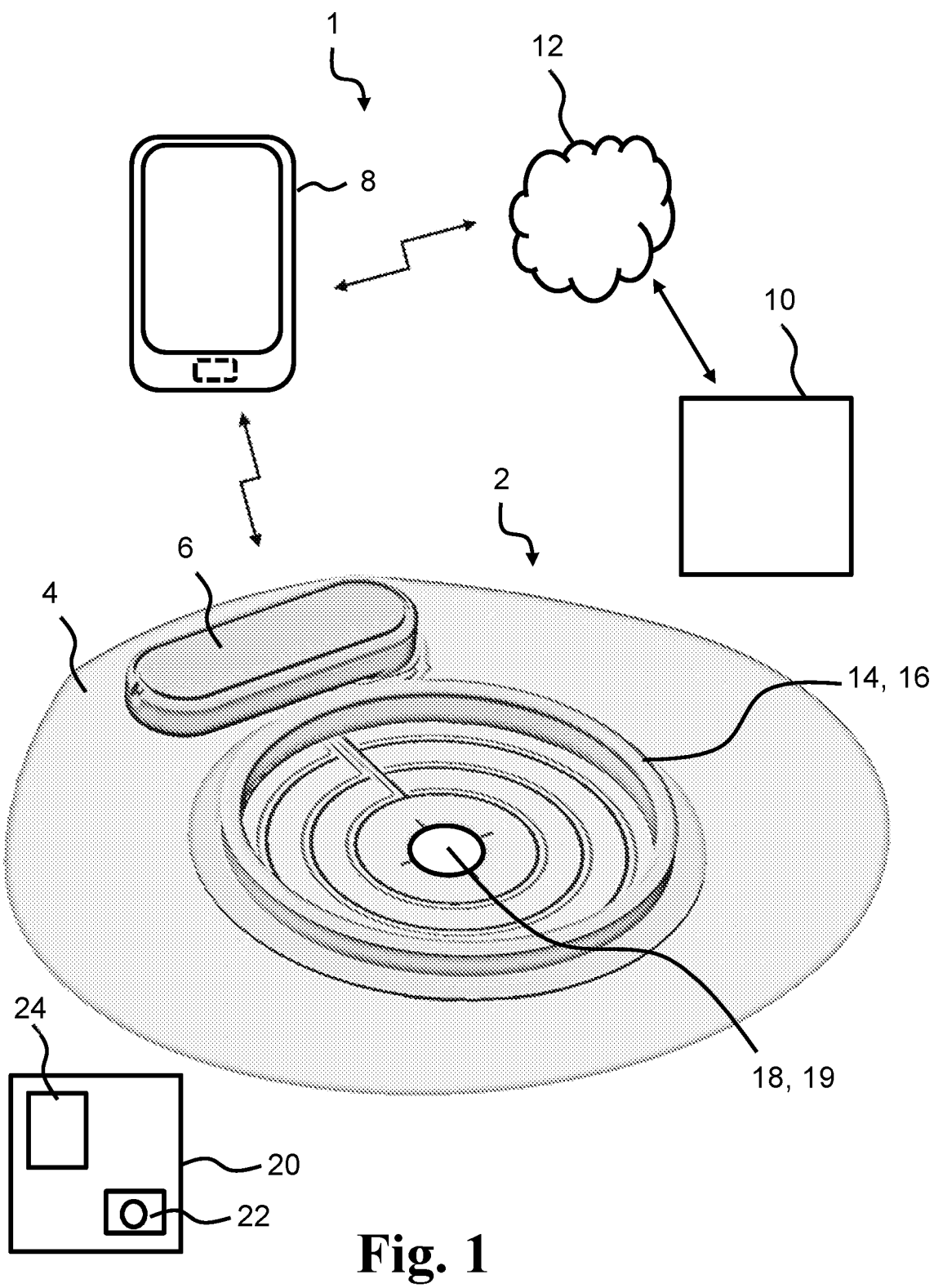
FIG. 1 illustrates an exemplary ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him—or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

A radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to an ostomy system and devices thereof, such as an ostomy appliance, a base plate for an ostomy appliance, a monitor device, and optionally one or more accessory devices. Further, methods related to the ostomy system and devices thereof are disclosed. An accessory device (also referred to as an external device) may be a mobile phone or other handheld device. An accessory device may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The ostomy system may comprise a server device. The server device may be operated and/or controlled by the ostomy appliance manufacturer and/or a service centre.

The present disclosure provides an ostomy system and devices thereof, such as an ostomy appliance, a base plate for an ostomy appliance, a monitor device, and optionally one or more accessory devices which either alone or together facilitate reliable determination of the nature, severity, and rapidness of moisture propagation in the adhesive material provided for attaching the base plate to the skin surface of a user. Depending on the nature of the pattern of moisture propagation in the adhesive, the ostomy system and devices thereof enable providing information to the user about the type of failure, and in turn enable providing an indication to the user of the severity and thus the remaining time frame for replacing the ostomy appliance without experiencing severe leakage and/or skin damage.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area.

The ostomy appliance includes a base plate, such as a monolithic, one-piece base plate, e.g. integrated with a sensor assembly part, or a base plate and a separate sensor assembly part, such as a sensor assembly part to be subsequently applied to a base plate. For example, to allow an arbitrary base plate, such as a conventional base plate, to achieve the features as described herein. Features as described with respect to the base plate herein may be provided by a sensor assembly part to be applied to a base plate, e.g. by the user. A sensor assembly part may be adapted to adhere to an ostomy plate.

A disclosed method of attaching a base plate to a user's stoma and/or skin surrounding the stoma, such as the peristomal skin area, may comprise attaching a sensor assembly part to a base plate and attaching the base plate, e.g. together with the attached sensor assembly part, to the user's stoma and/or skin surrounding the stoma, such as the peristomal skin area. Alternatively, the method of attaching the base plate to the user's stoma and/or skin surrounding the stoma may comprise attaching the sensor assembly part to the user's stoma and/or skin surrounding the stoma and attaching the base plate to the user's stoma and/or skin surrounding the stoma above the attached sensor assembly part.

A base plate and/or a sensor assembly part for an ostomy appliance is disclosed, the base plate and/or the sensor assembly part comprising a first adhesive layer with a proximal side configured for attachment of the base plate and/or the sensor assembly part to the skin surface of a user, the first adhesive layer having a stomal opening, such as a first adhesive stomal opening, with a center point; and a plurality of electrodes including a first leakage electrode, a second leakage electrode, and a third leakage electrode, wherein the plurality of electrodes is configured to detect presence of fluid on the proximal side of the first adhesive layer in a primary sensing zone and a secondary sensing zone. The primary sensing zone may be arranged in a primary angle space from the center point of the first adhesive layer and/or the secondary sensing zone may be arranged in a secondary angle space from the center point of the first adhesive layer. Alternatively or additionally, the primary sensing zone may be arranged in a primary radial space from the center point of the first adhesive layer and the secondary sensing zone may be arranged in a secondary radial space from the center point of the first adhesive layer Further, a monitor device for an ostomy system is disclosed. The ostomy system comprising an ostomy appliance with a base plate and/or a sensor assembly part, such as the base plate and/or sensor assembly part as also described herein, such as a base plate and/or sensor assembly part having a first adhesive layer with a proximal side configured for attachment of the base plate and/or the sensor assembly part to the skin surface of a user, the first adhesive layer having a stomal opening with a center point. The monitor device comprises a processor; memory; a first interface connected to the processor and the memory; and a second interface connected to the processor. The first interface is configured for obtaining ostomy data from the base plate and/or the sensor assembly part coupled to the first interface. The ostomy data comprises primary leakage ostomy data from a primary electrode set of the base plate and/or the sensor assembly part, and secondary leakage ostomy data from a secondary electrode set of the base plate and/or the sensor assembly part. The processor is configured to: obtain primary leakage parameter data based on the primary leakage ostomy data; obtain secondary leakage parameter data based on the secondary leakage ostomy data; detect presence of fluid on the proximal side of the first adhesive layer in a primary sensing zone based on the primary leakage parameter data, the primary sensing zone may be arranged in a primary angle space from the center point of the first adhesive layer and/or arranged in a primary radial space from the center point of the first adhesive layer; detect presence of fluid on the proximal side of the first adhesive layer in a secondary sensing zone based on the secondary leakage parameter data, the secondary sensing zone may be arranged in a secondary angle space from the center point of the first adhesive layer and/or arranged in a secondary radial space from the center point of the first adhesive layer; in accordance with a detection of presence of fluid in the primary sensing zone, transmit a primary leakage monitor signal comprising monitor data indicative of presence of fluid in the primary sensing zone via the second interface; and in accordance with a detection of presence of fluid in the secondary sensing zone, transmit a secondary leakage monitor signal comprising monitor data indicative of presence of fluid in the secondary sensing zone via the second interface.

Further, a method of monitoring a base plate and/or a sensor assembly part of an ostomy appliance is disclosed, the base plate and/or the sensor assembly part comprising a first adhesive layer and a plurality of electrodes, the first adhesive layer having a proximal side configured for attachment of the base plate and/or the sensor assembly part to the skin surface of a user and a stomal opening, such as a first adhesive stomal opening, with a center point, the plurality of electrodes including a first leakage electrode, a second leakage electrode, and a third leakage electrode. The method comprises obtaining a primary sensor signal (primary leakage ostomy data) from the first leakage electrode and the second leakage electrode; detecting presence of fluid on the proximal side in a primary sensing zone based on the primary sensor signal (primary leakage ostomy data); obtaining a secondary sensor signal (secondary leakage ostomy data) from the second leakage electrode and the third leakage electrode or from the first leakage electrode and the third leakage electrode; detecting presence of fluid on the proximal side in a secondary sensing zone based on the secondary sensor signal (secondary leakage ostomy data); and in accordance with detection of presence of fluid in the primary sensing zone and/or the secondary sensing zone, providing a leakage indicator indicative of the sensing zone in which presence of liquid has been detected. The method may be performed with a base plate and/or a sensor assembly part as disclosed herein.

The method may comprise obtaining a tertiary sensor signal (tertiary leakage ostomy data) from two leakage electrodes; detecting presence of fluid on the proximal side in a tertiary sensing zone based on the tertiary sensor signal (tertiary leakage ostomy data); and in accordance with detection of presence of fluid in the tertiary sensing zone, providing a leakage indicator indicative of the sensing zone in which presence of liquid has been detected.

The method may comprise obtaining a quaternary sensor signal (quaternary leakage ostomy data) from two leakage electrodes; detecting presence of fluid on the proximal side in a quaternary sensing zone based on the quaternary sensor signal (quaternary leakage ostomy data); and in accordance with detection of presence of fluid in the quaternary sensing zone, providing a leakage indicator indicative of the sensing zone in which presence of liquid has been detected.

The base plate and/or the sensor assembly part comprises a first adhesive layer. During use, the first adhesive layer adheres to the user's skin (peristomal area) and/or to additional seals, such as sealing paste, sealing tape and/or sealing ring. Thus, the first adhesive layer may be configured for attachment of the base plate and/or the sensor assembly part to the skin surface of a user. The first adhesive layer has a stomal opening, such as a first adhesive stomal opening, with a center point or is at least prepared for forming a stomal opening with a center point. A base plate and/or a sensor assembly part according to the present disclosure enables detection of presence and angular position of fluid or output on the proximal side of the first adhesive layer (between a skin surface of the user and the proximal surface of the first adhesive layer).

The first adhesive layer may be made of a first composition. The first composition may comprise one or more polyisobutenes and/or styrene-isoprene-styrene. The first composition may comprise one or more hydrocolloids. The first composition may comprise one or more water soluble or water swellable hydrocolloids.

The first composition may be a pressure sensitive adhesive composition suitable for medical purposes comprising a rubbery elastomeric base and one or more water soluble or water swellable hydrocolloids. The first composition may comprise one or more polybutenes, one or more styrene copolymers, one or more hydrocolloids, or any combination thereof. The combination of the adhesive properties of the polybutenes and the absorbing properties of the hydrocolloids renders the first composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the first composition are selected from naturally occurring hydrocolloids, semisynthetic hydrocolloids, and synthetic hydrocolloids. The first composition may comprise 20-60% hydrocolloids. A preferred hydrocolloid is carboxymethyl cellulose (CMC). The first composition may optionally contain other components, such as fillers, tackifiers, plasticizers, and other additives.

It is an advantage of the present disclosure that an optimum or improved use of an ostomy appliance is provided. In particular, the present disclosure facilitates that a base plate is not changed too late (leading to adhesive failure, leakage and/or skin damage), or at least that a user is informed that a leakage will happen, is happening, or has happened. Accordingly, the user or a health care professional is able to monitor and plan the use of the ostomy appliance.

Further, determination of moisture pattern types or angular leakage patterns is useful in helping to reduce the risk of a user experiencing leakage from an ostomy appliance. Further, determination of moisture pattern types and classification of operating states and/or leakage patterns of the ostomy appliance is further useful in helping reduce the risk of skin damage to a user.

The present disclosure provides an efficient, and easy-to-use ostomy appliance system with a high degree of comfort for a user.

The primary sensing zone of the base plate and/or the sensor assembly part may be arranged in a primary angle space from the center point of the first adhesive layer. The primary angle space may span a primary angle in the range from 45° to 315°, such as in the range from 45° to 135°. The primary angle may depend on the number of angular sensing zones on the base plate and/or the sensor assembly part. For example, the primary angle may be about 180°±15°, e.g. for a base plate and/or a sensor assembly part with two or more sensing zones. The primary angle may be about 120°±15°, e.g. for a base plate and/or a sensor assembly part with two, three or more sensing zones. The primary angle may be about 90°±15°, e.g. for a base plate and/or a sensor assembly part with two, three, four or more sensing zones.

Alternatively or additionally, the primary sensing zone may be arranged in a primary radial space from the center point of the first adhesive layer. The primary radial space may span a primary radius in the range from 10-50 mm, such as in the range from 10-25 mm, such as in the range from 19-20 mm. The primary radius may depend on the number of radial sensing zones on the base plate and/or the sensor assembly part.

The secondary sensing zone may be arranged in a secondary angle space from the center point of the first adhesive layer. The secondary angle space may span a secondary angle in the range from 45° to 315°, such as in the range from 45° to 135°. The secondary angle may depend on the number of angular sensing zones on the base plate and/or the sensor assembly part. For example, the secondary angle may be about 180°±15°, e.g. for a base plate and/or a sensor assembly part with two or more sensing zones. The secondary angle may be about 120°±15°, e.g. for a base plate and/or a sensor assembly part with two, three or more sensing zones. The secondary angle may be about 90°±15°, e.g. for a base plate and/or a sensor assembly part with two, three, four or more sensing zones.

Alternatively or additionally, the secondary sensing zone may be arranged in a secondary radial space from the center point of the first adhesive layer. The secondary radial space may span a secondary radius in the range from 15-50 mm, such as in the range from 20-30, such as in the range from 25-26 mm. The secondary radius may depend on the number of radial sensing zones on the base plate and/or the sensor assembly part. The secondary radius may be greater than the primary radius.

The plurality of electrodes may be configured to detect presence of fluid on the proximal side in a tertiary sensing zone. The tertiary sensing zone may be arranged in a tertiary angle space from the center point of the first adhesive layer.

The tertiary angle space may span a tertiary angle in the range from 45° to 315°, such as in the range from 45° to 180°, for example in the range from 45° to 135°. The tertiary angle may depend on the number of angular sensing zones on the base plate and/or the sensor assembly part. For example, the tertiary angle may be about 180°±15°, e.g. for a base plate and/or a sensor assembly part with three or more sensing zones. The tertiary angle may be about 120°±15°, e.g. for a base plate and/or a sensor assembly part with three or more sensing zones. The tertiary angle may be about 90°±15°, e.g. for a base plate and/or a sensor assembly part with three, four or more sensing zones.

Alternatively or additionally, the tertiary sensing zone may be arranged in a tertiary radial space from the center point of the first adhesive layer. The tertiary radial space may span a tertiary radius in the range from 15-50 mm, such as in the range from 25-50, such as in the range from 29-30 mm. The tertiary radius may depend on the number of radial sensing zones on the base plate and/or the sensor assembly part. The tertiary radius may be greater than the secondary radius and/or the primary radius.

The primary sensing zone and the secondary sensing zone may be separate sensing zones, i.e. non-overlapping. The primary sensing zone and the tertiary sensing zone may be separate sensing zones, i.e. non-overlapping. The secondary sensing zone and the tertiary sensing zone may be separate sensing zones, i.e. non-overlapping.

The primary sensing zone, the secondary sensing zone, and/or the tertiary sensing zone may cover electrodes embedded in the first adhesive layer as well as leakage electrodes being exposed to the surroundings. Thereby, the propagation or absorption of moisture in the first adhesive layer may be detected in one or more of the sensing zones, thereby providing for the determination of the direction of moisture propagation in the first adhesive layer. Likewise, output propagating between the skin of the wearer and the first adhesive layer may be determined by the exposed leakage electrodes. The leakage electrodes may be exposed by means of sensor point openings as described below.

The first leakage electrode may comprise one or more primary first sensing parts arranged in the primary sensing zone. The number of primary first sensing parts may be in the range from 3 to 10, e.g. 4, 5, 6 or 7. The number of primary first sensing parts may depend on the primary angle and/or the radial distance of primary first sensing parts from the center point. The first leakage electrode may comprise one or more tertiary first sensing parts arranged in the tertiary sensing zone. The number of tertiary first sensing parts may be in the range from 3 to 10, e.g. 4, 5, 6 or 7. The number of tertiary first sensing parts may depend on the tertiary angle and/or the radial distance of tertiary first sensing parts from the center point.

The second leakage electrode comprises one or more primary second sensing parts arranged in the primary sensing zone. The number of primary second sensing parts may be in the range from 3 to 10, e.g. 4, 5, 6 or 7. The number of primary second sensing parts may depend on the primary angle and/or the radial distance of primary second sensing parts from the center point. The second leakage electrode comprises one or more secondary second sensing parts arranged in the secondary sensing zone. The number of secondary second sensing parts may be in the range from 3 to 10, e.g. 4, 5, 6 or 7. The number of secondary second sensing parts may depend on the secondary angle and/or the radial distance of secondary second sensing parts from the center point.

The third leakage electrode may comprise one or more secondary third sensing parts arranged in the secondary sensing zone. The number of secondary third sensing parts may be in the range from 3 to 10, e.g. 4, 5, 6 or 7. The number of secondary third sensing parts may depend on the secondary angle and/or the radial distance of secondary third sensing parts from the center point. The third leakage electrode may comprise one or more tertiary third sensing parts arranged in the tertiary sensing zone. The number of tertiary third sensing parts may be in the range from 3 to 10, e.g. 4, 5, 6 or 7. The number of tertiary third sensing parts may depend on the tertiary angle and/or the radial distance of tertiary third sensing parts from the center point.

The first adhesive layer may have a plurality of sensor point openings. A sensor point opening of the first adhesive layer is configured to overlap a (sensing) part of a leakage electrode, e.g. to form a sensor point. Sensing parts of the first leakage electrode may be exposed to the proximal side of the first adhesive layer via sensor point openings in the first adhesive layer and/or masking element. Sensing parts of the second leakage electrode may be exposed to the proximal side of the first adhesive layer via sensor point openings in the first adhesive layer and/or masking element. Sensing parts of the third leakage electrode may be exposed to the proximal side of the first adhesive layer via sensor point openings in the first adhesive layer and/or masking element.

A distance between two neighbouring sensor point openings may be in the range from 1 mm to 20 mm.

A sensor point opening of the first adhesive layer may have a suitable shape and size facilitating access to a leakage electrode from the proximal side of the first adhesive layer. A sensor point opening the first adhesive layer may have a circular or oval shape. A sensor point opening the first adhesive layer may have a shape of a rectangle or square optionally with rounded corners.

A minimum extension of a sensor point opening of the first adhesive layer may be at least 0.5 mm, such as at least 1 mm. A sufficiently large minimum extension reduces the risk of the first adhesive layer, due to the materials flow capabilities, closing the sensor point opening or at least partly or fully covering the sensing part of the corresponding leakage electrode.

A maximum extension of a sensor point opening of the first adhesive layer may be less than 20 mm.

An exemplary sensor point opening of the first adhesive layer may have a minimum extension, e.g. measured radially from the center point, in the range from 1 mm to 4 mm and/or a maximum extension, e.g. measured circumferentially around the center point, in the range from 2 mm to 6 mm.

The sensor point openings of the first adhesive layer may comprise primary sensor point openings. The number of primary sensor point openings may depend on the primary angle and/or the radial distance of primary sensor point openings from the center point. In one or more exemplary base plates and/or sensor assembly parts, the number of primary sensor point openings is in the range from 5 to 20, such as in the range from 7 to 15. The primary sensor point openings may comprise one or more primary first sensor point openings and one or more primary second sensor point openings, the primary first sensor point openings configured to overlap (sensing) parts of a leakage electrode and the primary second sensor point openings configured to overlap (sensing) parts of another leakage electrode different from the leakage electrode at least partly overlapped by the primary first sensor point openings.

The sensor point openings of the first adhesive layer may comprise secondary sensor point openings. The number of secondary sensor point openings may depend on the secondary angle and/or the radial distance of secondary sensor point openings from the center point. In one or more exemplary base plates and/or sensor assembly parts, the number of secondary sensor point openings is in the range from 5 to 20, such as in the range from 7 to 15. The secondary sensor point openings may comprise one or more secondary first sensor point openings and one or more secondary second sensor point openings, the secondary first sensor point openings configured to overlap (sensing) parts of an electrode and the secondary second sensor point openings configured to overlap (sensing) parts of another electrode different from the electrode at least partly overlapped by the secondary first sensor point openings.

The sensor point openings of the first adhesive layer may comprise tertiary sensor point openings. The number of tertiary sensor point openings may depend on the tertiary angle and/or the radial distance of tertiary sensor point openings from the center point. In one or more exemplary base plates and/or sensor assembly parts, the number of tertiary sensor point openings is in the range from 5 to 20, such as in the range from 7 to 15. The tertiary sensor point openings may comprise one or more tertiary first sensor point openings and one or more tertiary third sensor point openings, the tertiary first sensor point openings configured to overlap (sensing) parts of a (first) leakage electrode and the tertiary third sensor point openings configured to overlap (sensing) parts of another (third) leakage electrode different from the electrode at least partly overlapped by the tertiary first sensor point openings.

The first adhesive layer may have a substantially uniform thickness. The first adhesive layer may have a thickness in the range from 0.1 mm to 1.5 mm, e.g. in the range from 0.2 mm to 1.2 mm, such as 0.8 mm or 1.0 mm.

The first adhesive layer may have a primary thickness in a primary part of the first adhesive layer, e.g. in a primary region within a primary radial distance or in a primary radial distance range from the center point of the stomal opening. The primary thickness may be in the range from 0.2 mm to 1.5 mm. such as about 1.0 mm. The primary radial distance may be in the range from 20 mm to 50 mm, such as in the range from 25 mm to 35 mm, e.g. 30 mm.

The first adhesive layer may have a secondary thickness in a secondary part of the first adhesive layer, e.g. in a secondary region outside a secondary radial distance or in a secondary radial distance range from the center point of the stomal opening. The secondary thickness may be in the range from 0.2 mm to 1.0 mm, such as about 0.5 mm. The secondary radial distance may be in the range from 20 mm to 50 mm, such as in the range from 25 mm to 35 mm, e.g. 30 mm.

The base plate and/or the sensor assembly part may comprise a second layer. The second layer may be an adhesive layer. The second layer may have a second radial extension that is larger than a first radial extension of the first adhesive layer at least in a first angular range of the base plate and/or the sensor assembly part. Accordingly, a part of a proximal surface of the second layer may be configured for attachment to the skin surface of a user. The part of a proximal surface of the second layer configured for attachment to the skin surface of a user is also denoted the skin attachment surface of the second adhesive layer. The second layer may have a stomal opening, such as a second layer stomal opening and/or a second adhesive stomal opening, with a center point.

The second adhesive layer may be made of a second composition. The second composition may comprise one or more polyisobutenes and/or styrene-isoprene-styrene. The second composition may comprise one or more hydrocolloids. The second composition may comprise one or more water soluble or water swellable hydrocolloids.

The second composition may be a pressure sensitive adhesive composition suitable for medical purposes comprising a rubbery elastomeric base and one or more water soluble or water swellable hydrocolloids. The second composition may comprise one or more polybutenes, one or more styrene copolymers, one or more hydrocolloids, or any combination thereof. The combination of the adhesive properties of the polybutenes and the absorbing properties of the hydrocolloids renders the second composition suitable for use in ostomy appliances. The styrene copolymer may for example be a styrene-butadiene-styrene block copolymer or a styrene-isoprene-styrene block copolymer. Preferably, one or more styrene-isoprene-styrene (SIS) block type copolymers are employed. The amount of styrene block-copolymer may be from 5% to 20% of the total adhesive composition. The butene component is suitably a conjugated butadiene polymer selected from polybutadiene, polyisoprene. The polybutenes are preferably present in an amount of from 35-50% of the total adhesive composition. Preferably, the polybutene is polyisobutylene (PIB). Suitable hydrocolloids for incorporation in the second composition are selected from naturally occurring hydrocolloids, semisynthetic hydrocolloids, and synthetic hydrocolloids. The second composition may comprise 20-60% hydrocolloids. A preferred hydrocolloid is carboxymethyl cellulose (CMC). The second composition may optionally contain other components, such as fillers, tackifiers, plasticizers, and other additives.

Different ratio of contents may change properties of the first and/or second adhesive layers. The second adhesive layer and the first adhesive layer may have different properties. The second adhesive layer (second composition) and the first adhesive layer (first composition) may have different ratios of polyisobutenes, styrene-isoprene-styrene, and/or hydrocolloids. For example, the second adhesive layer may provide a stronger attachment to the skin compared to attachment to the skin provided by the first adhesive layer. Alternatively, or additionally, the second adhesive layer may be thinner than the first adhesive layer. Alternatively, or additionally, the second adhesive layer may be less water and/or sweat absorbing than the first adhesive layer. Alternatively, or additionally, the second adhesive layer may be less moldable than the first adhesive layer. The second adhesive layer may provide a second barrier against leakage.

The second layer may have a substantially uniform thickness. The second layer may have a thickness in the range from 0.1 mm to 1.5 mm, e.g. in the range from 0.2 mm to 1.0 mm, such as 0.5 mm, 0.6 mm, or 0.7 mm.

In the present disclosure, a reference to ground electrode (or to fourth electrode part of the ground electrode) is a reference to the first leakage electrode. Thus, throughout the present disclosure the first leakage electrode is also referred to as or denoted ground electrode. In other words, the ground electrode acts as the first leakage electrode.

In the present disclosure, a reference to fourth electrode is a reference to the second leakage electrode. Thus, throughout the present disclosure the second leakage electrode is also referred to as or denoted fourth electrode. In other words, the fourth electrode acts as the second leakage electrode.

In the present disclosure, a reference to fifth electrode is a reference to the third leakage electrode. Thus, throughout the present disclosure the third leakage electrode is also referred to as or denoted fifth electrode. In other words, the fifth electrode acts as the third leakage electrode.

The base plate and/or the sensor assembly part may comprise one or more electrodes, such as a plurality of electrodes, such as two, three, four, five, six, seven or more electrodes. The sensor assembly part may be applied to the base plate, such as to provide the base plate with the one or more electrodes.

The electrodes, e.g. some or all the electrodes, may be arranged between the first adhesive layer and the second adhesive layer. The electrodes may be arranged in an electrode assembly, e.g. an electrode layer. An electrode comprises a connection part for connecting the electrodes to other components and/or interface terminals/terminal elements. An electrode may comprise one or more conductor parts and/or one or more sensing parts. A conductor part may be considered part of an electrode connecting two or more sensing parts, and/or connecting a sensing part with a connection part of the respective electrode. A sensing part may be considered a part of the electrode being suitable for sensing, e.g. liquid, such as liquid content, and/or output, such as output resulting from a leakage, or an imminent leakage. The sensing part may be suitable for sensing e.g. by its shape, said shape potentially being circular, oval, or rectangular. Thus, the conductor part may conduct a signal arising from the sensing part. An electrode may comprise alternating conductor parts and sensing parts. The electrode assembly may be arranged between the first adhesive layer and the second adhesive layer. The base plate and/or the sensor assembly part, e.g. the electrode assembly, may comprise a first electrode, a second electrode and optionally a third electrode. The base plate and/or the sensor assembly part, e.g. the electrode assembly, may comprise a fourth electrode and/or a fifth electrode. The base plate and/or the sensor assembly part, e.g. the electrode assembly, optionally comprises a sixth electrode. The base plate and/or the sensor assembly part, e.g. the electrode assembly, may comprise a ground electrode. The ground electrode may comprise a first electrode part. The first electrode part of the ground electrode may form a ground or reference for the first electrode. The ground electrode may comprise a second electrode part. The second electrode part of the ground electrode may form a ground or reference for the second electrode. The ground electrode may comprise a third electrode part. The third electrode part of the ground electrode may form a ground or reference for the third electrode. The ground electrode may comprise a fourth electrode part. The fourth electrode part of the ground electrode may form a ground or reference for the fourth electrode and/or the fifth electrode. The ground electrode may be configured as or form a (common) reference electrode for some or all of the other electrodes of the electrode assembly.

The electrodes are electrically conductive and may comprise one or more of metallic (e.g. silver, copper, gold, titanium, aluminium, stainless steel), ceramic (e.g. ITO), polymeric (e.g. PEDOT, PANI, PPy), and carbonaceous (e.g. carbon black, carbon nanotube, carbon fibre, graphene, graphite) materials.

The ground electrode may comprise a first electrode part and a second electrode part, the first electrode part forming the ground for the first electrode and the second electrode part forming the ground for the second electrode. The first electrode part may form a closed loop.

Two electrodes of the electrode assembly may form a sensor. The first leakage electrode and the second leakage electrode may form a primary leakage sensor or primary leakage electrode pair for detecting presence of fluid on the proximal side of the first adhesive layer in the primary sensing zone. The second leakage electrode and the third leakage electrode may form a secondary leakage sensor or secondary leakage electrode pair for detecting presence of fluid on the proximal side of the first adhesive layer in the secondary sensing zone. The first leakage electrode and the third leakage electrode may form a tertiary leakage sensor or tertiary leakage electrode pair for detecting presence of fluid on the proximal side of the first adhesive layer in the tertiary sensing zone.

An electrode may comprise a sensing part or a plurality of sensing parts, i.e. the part(s) of an electrode that are used for sensing. The first electrode may comprise a first sensing part, the first sensing part contacting the first adhesive layer and arranged at least partly annularly around the stomal opening. The first electrode may comprise a first conductor part insulated from the first adhesive layer, e.g. by a masking element arranged between the first conductor part and the first adhesive layer. The first sensing part may extend at least 270 degrees around the stomal opening, such as at least 300 degrees around the stomal opening. The first sensing part of the first electrode may be arranged at a first ground distance from the first electrode part of the ground electrode. The first ground distance may be less than 5 mm, such as less than 3 mm, e.g. about 1.0 mm.

The second electrode may comprise a second sensing part, the second sensing part contacting the first adhesive layer. The second sensing part may be arranged at least partly annularly around the stomal opening. The second sensing part may extend at least 270 degrees around the stomal opening, such as at least 300 degrees around the stomal opening. The second sensing part of the second electrode may be arranged at a second ground distance from the second electrode part of the ground electrode. The second ground distance may be less than 5 mm, such as less than 3 mm, e.g. about 1.0 mm.

The first sensing part may be arranged at a first radial distance from the center point and the second sensing part may be arranged at a second radial distance from the center point. The second radial distance may be larger than the first radial distance. The second electrode may comprise a second conductor part insulated from the first adhesive layer, e.g. by a masking element arranged between the second conductor part and the first adhesive layer. The first radial distance may vary as a function of an angular position with respect to a zero direction from the center point. The second radial distance may vary as a function of an angular position with respect to a zero direction from the center point. The zero direction may be defined as the vertical upward direction when the base plate and/or the sensor assembly part is in its intended wearing position on an upstanding user.

The first radial distance may be in the range from 5 mm to 40 mm, such as in the range from 10 mm to 25 mm, e.g. about 14 mm. The second radial distance may be in the range from 10 mm to 50 mm, such as in the range from 10 mm to 25 mm, e.g. about 18 mm.

The base plate and/or the sensor assembly part may comprise a third electrode comprising a third connection part. The ground electrode may form a ground for the third electrode. The ground electrode may comprise a third electrode part, the third electrode part forming the ground for the third electrode. The third electrode may comprise a third conductor part insulated from the first adhesive layer, e.g. by a masking element arranged between the third conductor part and the first adhesive layer. The third electrode may comprise a third sensing part, the third sensing part contacting the first adhesive layer. The third sensing part may be arranged at least partly annularly around the stomal opening. The third sensing part may be arranged at a third radial distance from the center point. The third radial distance may be larger than the first radial distance and/or larger than the second radial distance. The third radial distance may be in the range from 15 mm to 50 mm. such as in the range from 20 mm to 30 mm, e.g. about 26 mm. The third sensing part may extend at least 270 degrees around the stomal opening, such as at least 300 degrees around the stomal opening. The third sensing part of the third electrode may be arranged at a third ground distance from the third electrode part of the ground electrode. The third ground distance may be less than 5 mm, such as less than 3 mm, e.g. about 1.0 mm. A base plate and/or a sensor assembly part with a ground electrode, a first electrode, a second electrode, and a third electrode allows for a failsafe base plate and/or sensor assembly part in case e.g. the first electrode is cut or otherwise destroyed during preparation of the base plate and/or the sensor assembly part.

The base plate and/or the sensor assembly part comprises a second leakage electrode also denoted a fourth electrode, the fourth electrode comprising a fourth connection part.

The ground electrode (first leakage electrode) may form a ground for the fourth electrode. The ground electrode may comprise a fourth electrode part, the fourth electrode part forming the ground for the fourth electrode. The fourth electrode may comprise one or a plurality of fourth sensing parts, such as at least five fourth sensing parts. The fourth sensing parts may be distributed around the stomal opening or a center point thereof. The fourth sensing parts may be arranged at respective fourth radial distances from the center point. The fourth radial distance(s) may be larger than the third radial distance. The fourth radial distance(s) may be in the range from 25 mm to 50 mm, such as about 30 mm The base plate and/or the sensor assembly part may comprise a fifth electrode comprising a fifth connection part. The ground electrode may form a ground for the fifth electrode. The ground electrode may comprise a fifth electrode part, the fifth electrode part forming the ground for the fifth electrode. The fifth electrode may comprise one or a plurality of fifth sensing parts, such as at least five fifth sensing parts. The fifth sensing parts may be distributed around the stomal opening or a center point thereof. The fifth sensing parts may be arranged at respective fifth radial distances from the center point. The fifth radial distance may be larger than the third radial distance. The fifth radial distance may be larger than the fourth radial distance. The fifth radial distance(s) may be in the range from 25 mm to 50 mm, such as about 30 mm.

The first electrode may form an open loop. The second electrode may form an open loop and/or the third electrode may form an open loop. The fourth electrode may form an open loop. The fifth electrode may form an open loop. Open loop electrode(s) enables electrode arrangement in few or a single electrode layer.

The base plate and/or the sensor assembly part may comprise a second adhesive layer, wherein the plurality of electrodes is arranged between the first adhesive layer and the second adhesive layer.

The electrode assembly may comprise a support layer, also denoted a support film. One or more electrodes may be formed, e.g. printed, on the proximal side of the support layer. One or more electrodes may be formed, e.g. printed, on the distal side of the support layer. Thus, one or more electrodes may be arranged between the support layer and the first adhesive layer. The electrode assembly, such as the support layer of the electrode assembly, may have a stomal opening, such as an electrode assembly stomal opening and/or a support layer stomal opening, with a center point.

The support layer may comprise polymeric (e.g. polyurethane, PTFE, PVDF) and/or ceramic (e.g. alumina, silica) materials. In one or more exemplary base plates and/or sensor assembly parts, the support layer is made of thermoplastic polyurethane (TPU). The support layer material may be made of or comprise one or more of polyester, a thermoplastic elastomer (TPE), polyimide, polyimide, Ethylene-vinyl acetate (EVA), polyurea, and silicones.

Exemplary thermoplastic elastomers of the support layer are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part, such as the electrode assembly may comprise a masking element configured to insulate at least parts of the electrodes from the first adhesive layer of the base plate and/or of the sensor assembly part. The masking element may comprise one or more, such as a plurality of, sensor point openings. The sensor point openings may comprise primary sensor point openings and/or secondary sensor point openings. The sensor point openings may comprise tertiary sensor point opening(s). The sensor point openings may comprise quaternary sensor point opening(s). A sensor point opening of the masking element overlaps at least one electrode of the electrode assembly when seen in the axial direction, e.g. to form a sensor point. For example, a primary sensor point opening may overlap a (sensing) part of the ground electrode and/or a (sensing) part of the fourth electrode. A secondary sensor point opening may overlap a (sensing) part of the fourth electrode and/or a (sensing) part of the fifth electrode. A tertiary sensor point opening may overlap a (sensing) part of the fifth electrode and/or a (sensing) part of the ground electrode.

The masking element may comprise one or more, such as a plurality of, terminal openings. A terminal opening may overlap with one or more connection parts of electrodes. In one or more exemplary base plates, each terminal opening overlaps with a single connection part of an electrode.

The masking element may comprise polymeric (e.g. polyurethane, PTFE, PVDF) and/or ceramic (e.g. alumina, silica) materials. In one or more exemplary base plates and/or sensor assembly parts, the masking element is made of or comprises thermoplastic polyurethane (TPU). In one or more exemplary base plates and/or sensor assembly parts, the masking element is made of or comprises polyester. The masking element material may be made of or comprise one or more of polyester, a thermoplastic elastomer (TPE), polyamide, polyimide, Ethylene-vinyl acetate (EVA), polyurea, and silicones.

Exemplary thermoplastic elastomers of the masking element are styrenic block copolymers (TPS, TPE-s), thermoplastic polyolefin elastomers (TPO, TPE-o), thermoplastic Vulcanizates (TPV, TPE-v), thermoplastic polyurethanes (TPU), thermoplastic copolyester (TPC, TPE-E), and thermoplastic polyamides (TPA, TPE-A).

The base plate and/or the sensor assembly part may comprise a first intermediate element. The first intermediate element may be arranged between the electrodes/electrode layer and the first adhesive layer and/or between the second layer and the first adhesive layer. The first intermediate layer may be made of an insulating material.

The base plate and/or the sensor assembly part may comprise a release liner. The release liner is a protective layer that protects adhesive layer(s) during transport and storage and is peeled off by the user prior to applying the base plate on the skin. The release liner may have a stomal opening, such as a release liner stomal opening, with a center point.

The base plate and/or the sensor assembly part may comprise a top layer. The top layer is a protective layer protecting the adhesive layer(s) from external strains and stress when the user wears the ostomy appliance. The electrodes, e.g. some or all the electrodes, may be arranged between the first adhesive layer and the top layer. The top layer may have a stomal opening, such as a top layer stomal opening, with a center point. The top layer may have a thickness in the range from 0.01 mm to 1.0 mm, e.g. in the range from 0.02 mm to 0.2 mm, such as 0.04 mm. The top layer may have a stomal opening with a center point.

The base plate and/or the sensor assembly part may comprise a monitor interface. The monitor interface may be configured for electrically and/or mechanically connecting the ostomy appliance (base plate and/or sensor assembly part) to the monitor device. The monitor interface may be configured for wirelessly connecting the ostomy appliance (base plate and/or sensor assembly part) to the monitor device. Thus, the monitor interface of the base plate and/or the sensor assembly part may be configured to electrically and/or mechanically couple the ostomy appliance and the monitor device.

The monitor interface of the base plate and/or the sensor assembly part may comprise, e.g. as part of a first connector of the monitor interface, a coupling part for forming a mechanical connection, such as a releasable coupling between the monitor device and the base plate and/or the sensor assembly part. The coupling part may be configured to engage with a coupling part of the monitor device for releasably coupling the monitor device to the base plate and/or the sensor assembly part.

The monitor interface of the base plate and/or of the sensor assembly part may comprise, e.g. as part of a first connector of the monitor interface, a plurality of terminals, such as two, three, four, five, six, seven or more terminals, for forming electrical connections with respective terminals of the monitor device. The monitor interface may comprise a ground terminal element forming a ground terminal. The monitor interface may comprise a first terminal element forming a first terminal, a second terminal element forming a second terminal and optionally a third terminal element forming a third terminal. The monitor interface may comprise a fourth terminal element forming a fourth terminal and/or a fifth terminal element forming a fifth terminal. The monitor interface optionally comprises a sixth terminal element forming a sixth terminal. The terminal elements of the monitor interface may contact respective electrodes (connection parts) of the base plate and/or of the sensor assembly part, such as of the electrode assembly. The first intermediate element may be arranged between the terminal elements and the first adhesive layer. The first intermediate element may cover or overlap terminal element(s) of the base plate and/or of the sensor assembly part when seen in the axial direction. Thus, the first adhesive layer may be protected or experience more evenly distributed mechanical stress from the terminal elements of the base plate and/or of the sensor assembly part, in turn reducing the risk of terminal elements penetrating or otherwise damaging the first adhesive layer. The first intermediate element may protect or mechanically and/or electrically shield the first adhesive layer from the terminal elements of the base plate and/or of the sensor assembly part.

A terminal element, such as the ground terminal element, the first terminal element, the second terminal element, the third terminal element, the fourth terminal element, the fifth terminal element and/or the sixth terminal element, may comprise a distal end and a proximal end. A terminal element, such as the ground terminal element, the first terminal element, the second terminal element, the third terminal element, the fourth terminal element, the fifth terminal element and/or the sixth terminal element, may comprise a distal part, a centre part, and/or a proximal part. The distal part may be between the distal end and the centre part. The proximal part may be between the proximal end and the centre part. The proximal end/proximal part of a terminal element may contact a connection part of an electrode. A terminal element, such as the ground terminal element, the first terminal element, the second terminal element, the third terminal element, the fourth terminal element, the fifth terminal element and/or the sixth terminal element, may be gold plated copper.

The base plate may comprise a coupling ring or other coupling member for coupling an ostomy pouch to the base plate (two-part ostomy appliance). The center point may be defined as a center of the coupling ring.

The base plate and/or the sensor assembly part has a stomal opening with a center point. The stomal opening of the base plate and/or the sensor assembly part may be formed collectively of stomal opening(s) of the layers of the base plate and/or the sensor assembly part, such as of the top layer, the first adhesive layer, the second layer and/or the sensor assembly part. The stomal opening(s) of the layers of the base plate and/or the sensor assembly part, such as of the top layer, the first adhesive layer, the second layer and/or the sensor assembly part may be aligned to form the stomal opening of the base plate and/or the sensor assembly part. The stomal opening may be a through-going passage of the base plate and/or the sensor assembly part. The stomal opening may be arranged substantially in the center of the base plate and/or the sensor assembly part. The stomal opening(s) of the layers of the base plate and/or the sensor assembly part may be arranged substantially in the center of the respective layer. The stomal opening may be configured to receive a stoma of the user and/or the stomal opening may be configured to allow output from the stoma to pass through the stomal opening an into an ostomy pouch attached to the base plate. For example, the stomal opening may be configured to allow passage of output from a proximal side of the base plate and/or sensor assembly part to a distal side of the base plate and/or sensor assembly part. The size and/or shape of the stomal opening may typically be adjusted by the user or nurse before application of the ostomy appliance to accommodate the user's stoma. In one or more exemplary base plates, the user forms the stomal opening during preparation of the base plate for application.

The monitor device comprises a processor and one or more interfaces, such as a first interface and/or a second interface. The monitor device may comprise a memory for storing ostomy data.

In one or more exemplary monitor devices, the processor is configured to apply a processing scheme, the first interface is connected to the processor and the memory, and the first interface is configured for collecting ostomy data from the base plate and/or the sensor assembly part coupled to the first interface. The ostomy data may comprise one or more, such as all, of first ostomy data from a first electrode pair of the base plate and/or the sensor assembly part, second ostomy data from a second electrode pair of the base plate and/or the sensor assembly part, and third ostomy data from a third electrode pair of the base plate and/or the sensor assembly part. A second interface is connected to the processor. To apply a processing scheme may comprise one or more of obtain first parameter data based on the first ostomy data; obtain second parameter data based on the second ostomy data; and obtain third parameter data based on the third ostomy data. To apply a processing scheme may comprise determining an operating state of the base plate and/or of the sensor assembly part of the ostomy appliance based on one or more, such as all, of the first parameter data, the second parameter data and the third parameter data. The operating state may be indicative of a degree of radial erosion of the base plate, such as of the first adhesive layer, and/or an acute leakage risk for the ostomy appliance. The monitor device is configured to, in accordance with a determination that the operating state is a first operating state, transmit a first monitor signal comprising monitor data indicative of the first operating state of the base plate and/or the sensor assembly part via the second interface; and/or in accordance with a determination that the operating state is a second operating state, transmit a second monitor signal comprising monitor data indicative of the second operating state of the base plate and/or the sensor assembly part via the second interface.

In one or more exemplary monitor devices, the first operating state of the base plate and/or of the sensor assembly part corresponds to a situation wherein the first adhesive layer of the base plate and/or of the sensor assembly part has experienced a first degree of radial erosion, e.g. the first adhesive layer is eroded to a first radial distance of the first electrode pair but not to a second radial distance of the second electrode pair.

In one or more exemplary monitor devices, the second operating state of the base plate and/or of the sensor assembly part corresponds to a situation wherein the first adhesive layer of the base plate and/or of the sensor assembly part has experienced a second degree of radial erosion, e.g. the first adhesive layer is eroded to the second radial distance of the second electrode pair but not to a third radial distance of the third electrode pair.

To obtain first parameter data based on the first ostomy data may comprise determining one or more first parameters based on the first ostomy data. To obtain second parameter data based on the second ostomy data may comprise determining one or more second parameters based on the second ostomy data. To obtain third parameter data based on the third ostomy data may comprise determining one or more third parameters based on the third ostomy data. In one or more exemplary monitor devices, determination of an operating state may be based on one or more first parameters, such as first primary parameter and/or first secondary parameter of first parameter data. In one or more exemplary monitor devices, determination of an operating state may be based on one or more second parameters, such as second primary parameter and/or second secondary parameter of the second parameter data. In one or more exemplary monitor devices, determination of an operating state may be based on one or more third parameters, such as third primary parameter and/or third secondary parameter of the third parameter data. In one or more exemplary monitor devices, determination of an operating state may be based on one or more fourth parameters, such as fourth primary parameter and/or fourth secondary parameter of the fourth parameter data.

The first parameter data, the second parameter data, and the third parameter data may be indicative of resistance between the first electrode pair, the second electrode pair, and the third electrode pair, respectively.

The first parameter data, the second parameter data, and the third parameter data may be indicative of a rate of change in resistance between the first electrode pair, the second electrode pair, and the third electrode pair, respectively.

In one or more exemplary monitor devices, to determine an operating state of the base plate and/or the sensor assembly part is based on a first criteria set based on the first parameter data and/or the second parameter data, wherein the operating state is determined to be the first operating state if the first criteria set is satisfied. The first criteria set may comprise one or more first criteria based on one or more of first parameter data, second parameter data and third parameter data. The first criteria set may comprise a first primary criterion based on the first parameter data. The first criteria set may comprise a first secondary criterion based on the second parameter data. The first criteria set may comprise a first tertiary criterion based on the third parameter data.

In one or more exemplary monitor devices, to determine an operating state of the base plate and/or the sensor assembly part may be based on a first threshold set comprising one or a plurality of first threshold values. The first threshold set may comprise one or a plurality of threshold values, e.g. to be applied in the first criteria set. The first threshold set may comprise a first primary threshold value. The first threshold set may comprise a first secondary threshold value. The first threshold set may comprise a first tertiary threshold value.

The first criteria set may be given by (P_1_1<TH_1_1), (P_2_1>TH_1_2), and (P_3_1>TH_1_3), wherein P_1_1 is a first primary parameter based on the first parameter data, TH_1_1 is a first primary threshold value, P_2_1 is a second primary parameter based on the second parameter data, TH_1_2 is a first secondary threshold value, P_3_1 is a third primary parameter based on the third parameter data, and TH_1_3 is a first tertiary threshold value, and wherein the first operating state is indicative of low degree of radial erosion on the base plate and/or the sensor assembly part. The first threshold values (TH_1_1, TH_1_2 and TH_1_3) may be the same or different, e.g.

depending on the electrode configuration of the base plate and/or the sensor assembly part. The first tertiary criterion (P_3_1<TH_1_3) may be omitted in the first criteria set.

The first primary parameter P_1_1 may be indicative of the resistance between the first electrode pair (first electrode and first electrode part of the ground electrode) of the base plate and/or the sensor assembly part.

The second primary parameter may be indicative of the resistance between the second electrode pair (second electrode and second electrode part of the ground electrode) of the base plate and/or the sensor assembly part.

The third primary parameter may be indicative of resistance between the third electrode pair (third electrode and third electrode part of the ground electrode) of the base plate and/or the sensor assembly part.

In one or more exemplary monitor devices, to determine an operating state of the base plate and/or the sensor assembly part is based on a second criteria set based on the second parameter data and/or the third parameter data, wherein the operating state is determined to be the second operating state if the second criteria set is satisfied. The second criteria set may be based on the first parameter data.

The second criteria set may comprise one or more second criteria based on one or more of first parameter data, second parameter data and third parameter data. The second criteria set may comprise a second primary criterion based on the first parameter data. The second criteria set may comprise a second secondary criterion based on the second parameter data. The second criteria set may comprise a second tertiary criterion based on the third parameter data.

In one or more exemplary monitor devices, to determine an operating state of the base plate and/or the sensor assembly part is based on a second threshold set comprising one or a plurality of second threshold values. The second threshold set may comprise one or a plurality of threshold values, e.g. to be applied in the second criteria set. The second threshold set may comprise a second primary threshold value. The second threshold set may comprise a second secondary threshold value. The second threshold set may comprise a second tertiary threshold value.

The second criteria set may be given by (P_1_1<TH_2_1), (P_2_1<TH_2_2), and (P_3_1>TH_2_3)

wherein P_1_1 is a first primary parameter based on the first parameter data and indicative of the resistance between the first electrode pair, TH_2_1 is a second primary threshold value, P_2_1 is a second primary parameter based on the second parameter data and indicative of the resistance between the second electrode pair, TH_2_2 is a second secondary threshold value, P_3_1 is a third primary parameter based on the third parameter data and indicative of the resistance between the third electrode pair, TH_2_3 is a second tertiary threshold value, and wherein the second operating state is indicative of medium degree of radial erosion on the base plate and/or the sensor assembly part. The second threshold values (TH_2_1, TH_2_2 and TH_2_3) may be the same or different, e.g. depending on the electrode configuration of the base plate and/or the sensor assembly part. The second primary criterion (P_1_1<TH_2_1) and/or the second tertiary criterion (P_3_1>TH_2_3) may be omitted in the second criteria set.

In one or more exemplary monitor devices, to determine an operating state of the base plate and/or the sensor assembly part is based on a default criteria set based on the first parameter data, wherein the operating state is determined to be the default operating state if the default criteria set is satisfied, and in accordance with a determination that the operating state is the default operating state, transmit a default monitor signal comprising monitor data indicative of the default operating state of the ostomy appliance.

The default criteria set may be given by (P_1_1>TH_D_1), (P_2_1>TH_D_2), and (P_3_1>TH_D_3)

wherein P_1_1 is a first primary parameter based on the first parameter data and indicative of the resistance between the first electrode pair, TH_D_1 is a default primary threshold value, P_2_1 is a second primary parameter based on the second parameter data and indicative of the resistance between the second electrode pair, TH_D_2 is a default secondary threshold value, P_3_1 is a third primary parameter based on the third parameter data and indicative of the resistance between the third electrode pair, TH_D_3 is a default tertiary threshold value, and wherein the default operating state is indicative of very low or no degree of radial erosion on the base plate and/or the sensor assembly part. The default threshold values (TH_D_1, TH_D_2 and TH_D_3) may be the same or different, e.g. depending on the electrode configuration of the base plate and/or the sensor assembly part.

In one or more exemplary monitor devices, to determine an operating state of the base plate and/or the sensor assembly part is based on a third criteria set based on the third parameter data, wherein the operating state is determined to be the third operating state if the third criteria set is satisfied, and in accordance with a determination that the operating state is the third operating state, transmit a third monitor signal comprising monitor data indicative of the third operating state of the ostomy appliance.

In one or more exemplary monitor devices, the third operating state of the base plate and/or of the sensor assembly part corresponds to a situation wherein the first adhesive layer of the base plate and/or of the sensor assembly part has experienced a third degree of radial erosion, e.g. the first adhesive layer is eroded to the third radial distance of the third electrode pair.

The third criteria set may be given by (P_1_1<TH_3_1), (P_2_1<TH_3_2), and (P_3_1<TH_3_3)

wherein P_1_1 is a first primary parameter based on the first parameter data and indicative of the resistance between the first electrode pair, TH_3_1 is a third primary threshold value, P_2_1 is a second primary parameter based on the second parameter data and indicative of the resistance between the second electrode pair, TH_3_2 is a third secondary threshold value, P_3_1 is a third primary parameter based on the third parameter data and indicative of the resistance between the third electrode pair, TH_3_3 is a third tertiary threshold value, and wherein the third operating state is indicative of high degree of radial erosion on the base plate and/or the sensor assembly part. The third threshold values (TH_3_1, TH_3_2 and TH_3_3) may be the same or different, e.g. depending on the electrode configuration of the base plate and/or the sensor assembly part. The third primary criterion ($P\_1\_1 < TH\_3\_1$) and/or the third secondary criterion ($P\_2\_1 < TH\_3\_2$) may be omitted in the third criteria set.

In one or more exemplary monitor devices, the ostomy data comprises fourth ostomy data from a fourth electrode pair (first leakage electrode and second leakage electrode) of the base plate and/or the sensor assembly part. To apply a processing scheme may comprise to obtain fourth parameter data based on the fourth ostomy data, and determine an operating state of the base plate and/or the sensor assembly part of the ostomy appliance based on the fourth parameter data. The monitor device may be configured to, in accordance with a determination that the operating state is a fourth operating state, transmit a fourth monitor signal comprising monitor data indicative of the fourth operating state of the ostomy appliance.

In one or more exemplary monitor devices, the fourth operating state of the base plate and/or the sensor assembly part corresponds to a situation, wherein the fourth electrode pair detects fluid, such as output, between the distal surface of first adhesive layer and the skin of the user at a fourth radial distance, and thus there is a high risk of leakage from the ostomy appliance in the fourth operating state.

The fourth criteria set may be given by $$(P\_4\_1 < TH\_4\_4)$$

wherein $P\_4\_1$ is a fourth primary parameter based on the fourth parameter data and indicative of the resistance between the fourth electrode pair and $TH\_4\_4$ is a fourth quaternary threshold value, and wherein the fourth operating state is indicative of high risk of leakage from the ostomy appliance.

In one or more exemplary monitor devices, the ostomy data comprises leakage ostomy data from one or more electrode pairs of leakage electrodes of the base plate and/or the sensor assembly part. The leakage ostomy data may comprise primary leakage ostomy data, e.g. from the first leakage electrode and the second leakage electrode. The leakage ostomy data may comprise secondary leakage ostomy data, e.g. from the second leakage electrode and the third leakage electrode. The leakage ostomy data may comprise tertiary leakage ostomy data, e.g. from the first leakage electrode and the third leakage electrode.

To apply a processing scheme may comprise to obtain primary leakage parameter data based on primary leakage ostomy data of the leakage ostomy data, and determine an operating state of the base plate and/or the sensor assembly part of the ostomy appliance based on the primary leakage parameter data. The monitor device may be configured to, in accordance with a determination that the operating state is a primary leakage operating state, transmit a primary leakage monitor signal comprising monitor data indicative of the primary leakage operating state of the ostomy appliance.

In one or more exemplary monitor devices, the primary leakage operating state of the base plate and/or the sensor assembly part corresponds to a situation, wherein the first leakage and second leakage electrode detect fluid, such as output, between the distal surface of first adhesive layer and the skin of the user in the primary sensing zone, and thus there is a high risk of leakage from the ostomy appliance in the primary leakage operating state. The primary leakage monitor signal may be indicative of a high risk of leakage in the primary sensing zone.

The primary leakage criteria set may be given by $$(P\_PL < TH\_PL)$$

wherein $P\_PL$ is a primary leakage parameter based on the primary leakage parameter data and indicative of the resistance between the first leakage electrode and the second leakage electrode, $TH\_PL$ is a primary leakage threshold value. The primary leakage operating state may be indicative of high risk of leakage from the primary sensing zone of the ostomy appliance.

To apply a processing scheme may comprise to obtain secondary leakage parameter data based on secondary leakage ostomy data of the leakage ostomy data, and determine an operating state of the base plate and/or the sensor assembly part of the ostomy appliance based on the secondary leakage parameter data. The monitor device may be configured to, in accordance with a determination that the operating state is a secondary leakage operating state, transmit a secondary leakage monitor signal comprising monitor data indicative of the secondary leakage operating state of the ostomy appliance.

In one or more exemplary monitor devices, the secondary leakage operating state of the base plate and/or the sensor assembly part corresponds to a situation, wherein the second leakage electrode and third leakage electrode detect fluid, such as output, between the distal surface of first adhesive layer and the skin of the user in the secondary sensing zone, and thus there is a high risk of leakage from the ostomy appliance in the secondary leakage operating state. The secondary leakage monitor signal may be indicative of a high risk of leakage in the secondary sensing zone.

The secondary leakage criteria set may be given by $$(P\_SL < TH\_SL)$$

wherein $P\_SL$ is a secondary leakage parameter based on the secondary leakage parameter data. The secondary leakage parameter may be indicative of the resistance between the second leakage electrode and the third leakage electrode, see e.g. FIG. 11. The secondary leakage parameter may be indicative of the resistance between the first leakage electrode and the third leakage electrode, see e.g. FIG. 12. $TH\_SL$ is a secondary leakage threshold value, and the secondary leakage operating state is indicative of high risk of leakage from the secondary sensing zone of the ostomy appliance.

To apply a processing scheme may comprise to obtain tertiary leakage parameter data based on tertiary leakage ostomy data of the leakage ostomy data, and determine an operating state of the base plate and/or the sensor assembly part of the ostomy appliance based on the tertiary leakage parameter data. The monitor device may be configured to, in accordance with a determination that the operating state is a tertiary leakage operating state, transmit a tertiary leakage monitor signal comprising monitor data indicative of the tertiary leakage operating state of the ostomy appliance.

In one or more exemplary monitor devices, the tertiary leakage operating state of the base plate and/or the sensor assembly part corresponds to a situation, wherein the first leakage electrode and third leakage electrode detect fluid, such as output, between the distal surface of first adhesive layer and the skin of the user in the tertiary sensing zone, and thus there is a high risk of leakage from the ostomy appliance in the tertiary leakage operating state. The tertiary leakage monitor signal may be indicative of a high risk of leakage in the tertiary sensing zone.

The tertiary leakage criteria set may be given by $$(P\_TL < TH\_TL)$$

wherein $P\_TL$ is a tertiary leakage parameter based on the tertiary leakage parameter data and indicative of the resistance between the first leakage electrode and the third leakage electrode, TH_TL is a tertiary leakage threshold value, and wherein the tertiary leakage operating state is indicative of high risk of leakage from the tertiary sensing zone of the ostomy appliance.

The primary leakage threshold value, the secondary leakage threshold value, and the tertiary leakage threshold value may be the same or may be different.

The monitor device comprises a monitor device housing optionally made of a plastic material. The monitor device housing may be an elongate housing having a first end and a second end. The monitor device housing may have a length or maximum extension along a longitudinal axis in the range from 1 cm to 15 cm. The monitor device housing may have a width or maximum extension perpendicular to the longitudinal axis in the range from 0.5 cm to 3 cm. The monitor device housing may be curve-shaped. Additionally or alternatively, the monitor device may be rigid or flexible.

The monitor device comprises a first interface. The first interface may be configured as an appliance interface for electrically and/or mechanically connecting the monitor device to the ostomy appliance. Thus, the appliance interface is configured to electrically and/or mechanically couple the monitor device and the ostomy appliance. The first interface may be configured as an accessory device interface for electrically and/or mechanically connecting the monitor device to an accessory device, such as a docking station. The first interface may be configured for coupling to a docking station of the ostomy system, e.g. for charging the monitor device and/or for data transfer between the monitor device and the docking station.

The first interface of the monitor device may comprise a plurality of terminals, such as two, three, four, five, six, seven or more terminals, for forming electrical connections with respective terminals and/or electrodes of the ostomy appliance. One or more terminals of the first interface may be configured for forming electrical connections with an accessory device, e.g. with respective terminals of a docking station. The first interface may comprise a ground terminal. The first interface may comprise a first terminal, a second terminal and optionally a third terminal. The first interface may comprise a fourth terminal and/or a fifth terminal. The first interface optionally comprises a sixth terminal. In one or more exemplary monitor devices, the first interface has M terminals, wherein M is an integer in the range from 4 to 8.

The first interface of the monitor device may comprise a coupling part for forming a mechanical connection, such as a releasable coupling between the monitor device and the base plate and/or the sensor assembly part. The coupling part and the terminals of the first interface form (at least part of) a first connector of the monitor device.

The monitor device comprises a power unit for powering the monitor device. The power unit may comprise a battery. The power unit may comprise charging circuitry connected to the battery and terminals of the first interface for charging the battery via the first interface, e.g. the first connector. The first interface may comprise separate charging terminal(s) for charging the battery. Additionally or alternatively, the sensor terminal may change its function if the charging voltage is sensed at relevant terminals.

The monitor device may comprise a sensor unit with one or more sensor. The sensor unit is connected to the processor for feeding sensor data to the processor. The sensor unit may comprise an accelerometer for sensing acceleration and provision of acceleration data to the processor. The sensor unit may comprise a temperature sensor for provision of temperature data to the processor.

The monitor device comprises a second interface connected to the processor. The second interface may be configured as an accessory interface for connecting, e.g. wirelessly connecting, the monitor device to one or more accessory devices. The second interface may comprise an antenna and a wireless transceiver, e.g. configured for wireless communication at frequencies in the range from 2.4 to 2.5 GHz. The wireless transceiver may be a Bluetooth transceiver, i.e. the wireless transceiver may be configured for wireless communication according to Bluetooth protocol, e.g. Bluetooth Low Energy, Bluetooth 4.0, Bluetooth 5. The second interface optionally comprises a loudspeaker and/or a haptic feedback element for provision of an audio signal and/or haptic feedback to the user, respectively.

The monitor device may be electrically coupled to the plurality of electrodes of the base plate and/or the sensor assembly part. For example, the monitor device may be couplable, such as releasably couplable, to the plurality of electrodes of the base plate and/or the sensor assembly part. The monitor device may be configured to measure one or more resistances between the plurality of electrodes, and detect the leakage of output based on the measured one or more resistances.

In one or more exemplary ostomy systems, the monitor device forms an integrated part of the ostomy appliance, e.g. the monitor device may form an integrated part of a base plate and/or a sensor assembly part of the ostomy appliance.

The ostomy system may comprise a docking station forming an alternative/additional accessory device of the ostomy system. The docking station may be configured to electrically and/or mechanically couple the monitor device to the docking station.

The docking station may comprise a docking monitor interface. The docking monitor interface may be configured for electrically and/or mechanically connecting the monitor device to the docking station. The docking monitor interface may be configured for wirelessly connecting the monitor device to the docking station. The docking monitor interface of the docking station may be configured to electrically and/or mechanically couple the docking station and the monitor device.

The docking monitor interface of the docking station may comprise, e.g. as part of a first connector of the docking monitor interface, a coupling part for forming a mechanical connection, such as a releasable coupling between the monitor device and the docking station. The coupling part may be configured to engage with a coupling part of the monitor device for releasably coupling the monitor device to the docking station.

The docking monitor interface of the docking station may comprise, e.g. as part of a first connector of the docking monitor interface, a plurality of terminals, such as two, three, four, five, six, seven or more terminals, for forming electrical connections with respective terminals of the monitor device. The docking monitor interface may comprise a ground terminal. The docking monitor interface may comprise a first terminal and/or a second terminal. The docking station may comprise a third terminal. The docking monitor interface may comprise a fourth terminal and/or a fifth terminal. The docking monitor interface optionally comprises a sixth terminal.

FIG. 1 illustrates an exemplary ostomy system. The ostomy system 1 comprises an ostomy appliance 2 including a base plate 4. The base plate 4 is adapted to support an ostomy pouch (not shown). Further, the ostomy system 1 comprises a monitor device 6 and an accessory device 8 (mobile telephone). The monitor device 6 is connectable to the base plate 4 via respective first connectors of the monitor device 6 and base plate 4. The monitor device 6 is configured for wireless communication with the accessory device 8. Optionally, the accessory device 8 is configured to communicate with a server device 10 of the ostomy system 1, e.g. via network 12. The server device 10 may be operated and/or controlled by the ostomy appliance manufacturer and/or a service centre. Ostomy data or parameter data based on the ostomy data are obtained from electrodes/sensors of the ostomy appliance 2 with the monitor device 6. The monitor device 6 processes the ostomy data and/or parameter data based on the ostomy data. Based on the processed ostomy data, the monitor device 6 may determine what monitor data that are transmitted to the accessory device 8. In the illustrated ostomy system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine and transmit monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a center point 19. The size and/or shape of the stomal opening 18 is typically adjusted by the user or nurse before application of the ostomy appliance to accommodate the user's stoma.

The ostomy system 1 optionally comprises a docking station 20 forming an alternative/additional accessory device of the ostomy system 1. The docking station 20 comprises a docking monitor interface including a first connector 22 configured for electrically and/or mechanically connecting the monitor device 6 to the docking station 20. The docking monitor interface may be configured for wirelessly connecting the monitor device to the docking station. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
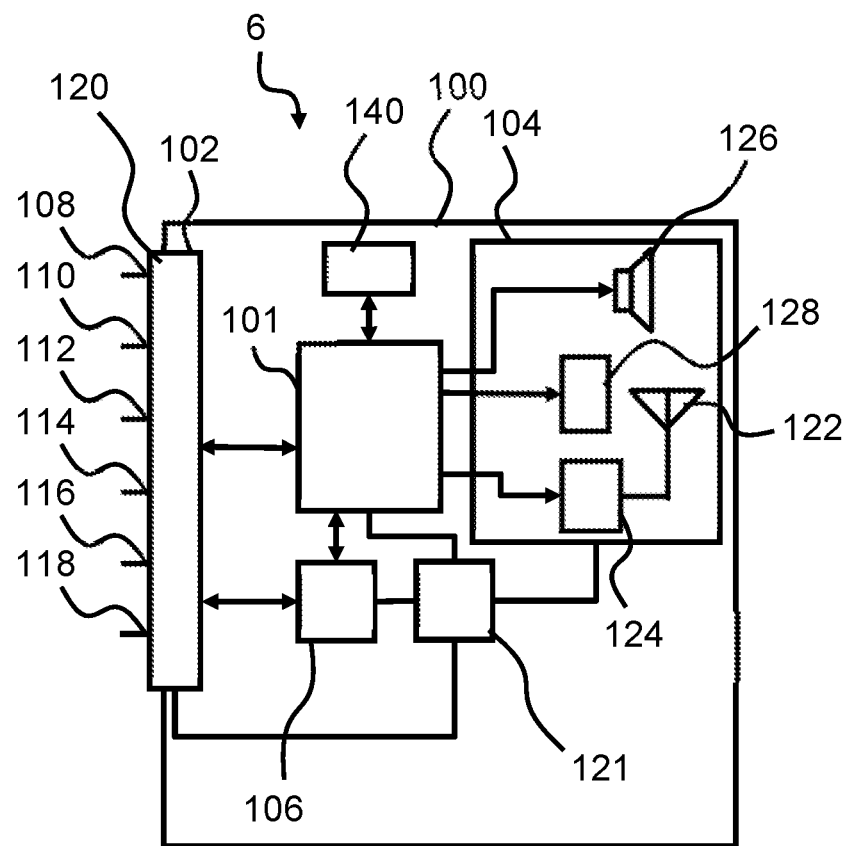
FIG. 2 illustrates an exemplary monitor device of the ostomy system.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106 for storing ostomy data and/or parameter data based on the ostomy data. The memory 106 is connected to the processor 101 and/or the first interface 102.

The first interface 102 is configured as an appliance interface for electrically and/or mechanically connecting the monitor device 6 to the ostomy appliance, e.g. ostomy appliance 2. The first interface 102 comprises a plurality of terminals for forming electrical connections with respective terminals of the ostomy appliance 2 (base plate 4). The first interface 102 comprises a ground terminal 108, a first terminal 110, a second terminal 112 and a third terminal 114. The first interface 102 optionally comprises a fourth terminal 116 and a fifth terminal 118. The first interface 102 of the monitor device 6 comprises a coupling part 120 for forming a mechanical connection, such as a releasable coupling between the monitor device and the base plate. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, the second interface 104, and memory 106. The power unit comprises a battery and charging circuitry. The charging circuitry is connected to the battery and terminals of the first interface 102 for charging the battery via terminals of the first interface, e.g. terminals of the first connector.

The second interface 104 of monitor device is configured as an accessory interface for connecting the monitor device 6 to one or more accessory devices such as accessory device 8. The second interface 104 comprises an antenna 122 and a wireless transceiver 124 configured for wireless communication with accessory device(s). Optionally, the second interface 104 comprises a loudspeaker 126 and/or a haptic feedback element 128 for provision of respective audio signal and/or haptic feedback to the user.

The monitor device 6 optionally comprises a sensor unit 140 connected to the processor 101. For example, the sensor unit 140 may comprise a temperature sensor for feeding temperature data to the processor and/or a G-sensor or accelerometer for feeding acceleration data to the processor 101. Additionally or alternatively, the sensor unit 140 comprises a humidity sensor and/or an acoustic sensor. The sensor unit 140 may comprise alternative and/or additional sensors suitable and/or relevant to an ostomy system as described.

The processor 101 is configured to apply a processing scheme, and the first interface 102 is configured for collecting ostomy data from the base plate and/or the sensor assembly part coupled to the first interface, the ostomy data comprising leakage ostomy data from leakage electrodes of the ostomy appliance. The ostomy data optionally comprises first ostomy data from a first electrode pair of the base plate and/or the sensor assembly part, second ostomy data from a second electrode pair of the base plate and/or the sensor assembly part, and/or third ostomy data from a third electrode pair of the base plate and/or the sensor assembly part. The ostomy data may be stored in the memory 106 and/or processed in the processor 101 in order to obtain parameter data. The parameter data may be stored in the memory 106. The processor 101 is configured to apply a processing scheme, wherein to apply a processing scheme comprises obtain primary leakage parameter data based on primary leakage ostomy data; obtain secondary leakage parameter data based on secondary leakage ostomy data; and obtain tertiary leakage parameter data based on tertiary leakage ostomy data. Optionally the processing scheme comprises obtain first parameter data based on the first ostomy data; obtain second parameter data based on the second ostomy data; obtain third parameter data based on the third ostomy data. In other words, the processor 101 may be configured to obtain first, second and third parameter data based on respective first, second and third ostomy data. To apply a processing scheme comprises to determine an operating state of the base plate and/or the sensor assembly part of the ostomy appliance based on one or more, e.g. all, of primary leakage parameter data, secondary leakage parameter data, and tertiary leakage parameter data, wherein the operating state is indicative an acute leakage risk in a sensing zone for the ostomy appliance. The monitor device 6 is configured to, in accordance with a determination that the operating state is a primary leakage operating state, transmit a primary leakage monitor signal comprising monitor data indicative of the primary leakage operating state of the base plate and/or the sensor assembly part via the second interface; and in accordance with a determination that the operating state is a secondary leakage operating state, transmit a secondary leakage monitor signal comprising monitor data indicative of the secondary leakage operating state of the base plate and/or the sensor assembly part via the second interface. The monitor device 6 may be configured to, in accordance with a determination that the operating state is a tertiary leakage operating state, transmit a tertiary leakage monitor signal comprising monitor data indicative of the tertiary leakage operating state of the base plate and/or the sensor assembly part via the second interface.

Figure 3:
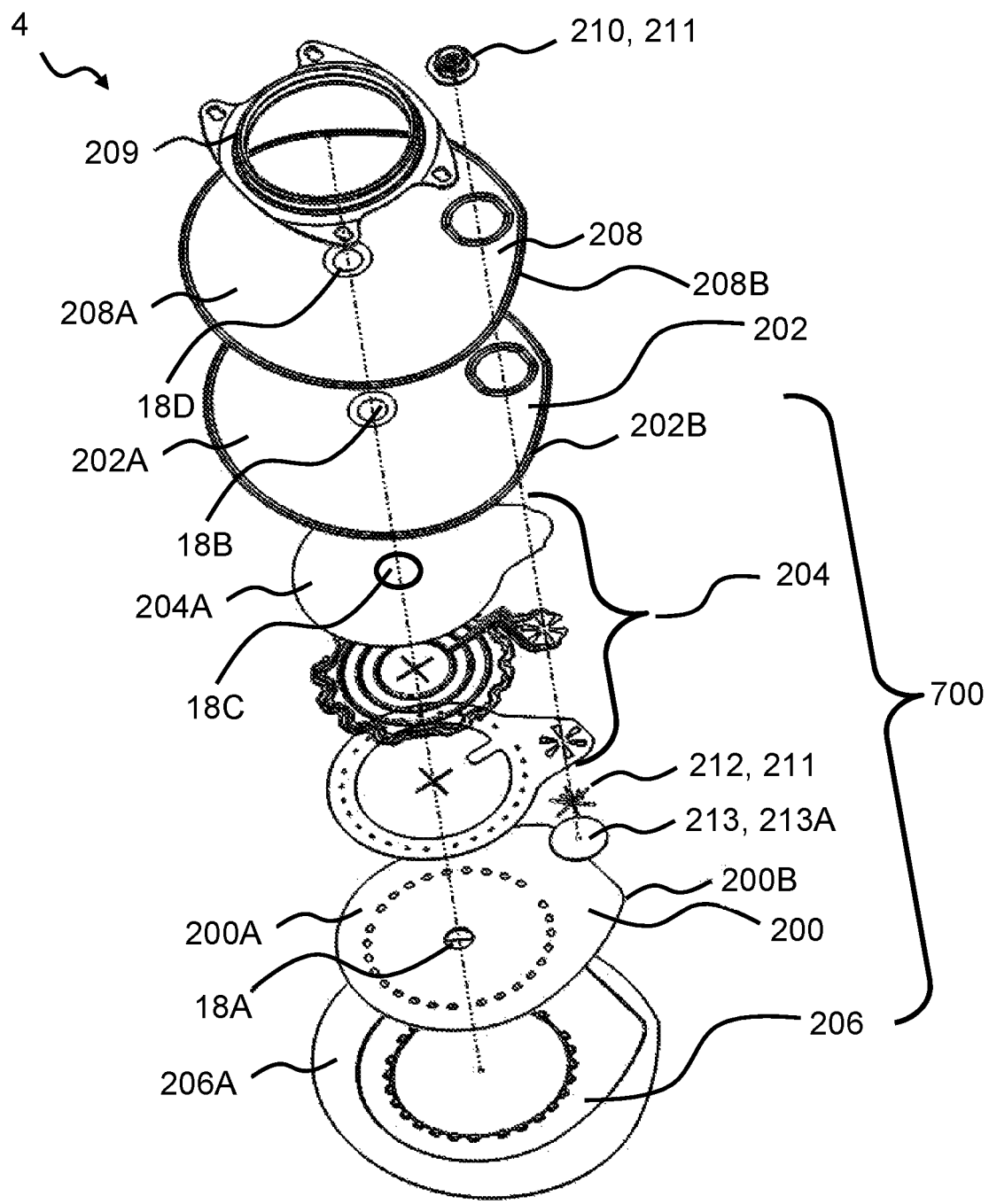
FIG. 3 is an exploded view of a base plate of an ostomy appliance.

FIG. 3 illustrates an exploded view of an exemplary base plate of an ostomy appliance. The base plate 4 comprises a first adhesive layer 200 with a stomal opening 18A. During use, a proximal surface of the first adhesive layer 200 adheres to the user's skin in the peristomal area and/or to additional seals, such as sealing paste, sealing tape and/or sealing ring. The base plate 4 optionally comprises a second adhesive layer 202, also denoted rim adhesive layer, with a stomal opening 18B. The base plate 4 comprises a plurality of electrodes arranged in an electrode assembly 204. The electrode assembly 204 is arranged between the first adhesive layer 200 and the second adhesive layer 202. The electrode assembly 204 comprises a support layer with stomal opening 18C and electrodes formed on a proximal surface of the support layer. The base plate 4 comprises a release liner 206 that is peeled off by the user prior to applying the base plate 4 on the skin. The base plate 4 comprises a top layer 208 with a stomal opening 18D and a coupling ring 209 for coupling an ostomy pouch to the base plate 4. The top layer 208 is a protective layer protecting the second adhesive layer 202 from external strains and stress during use.

The base plate 4 comprises a monitor interface. The monitor interface is configured for electrically and/or mechanically connecting the ostomy appliance (base plate 4) to the monitor device. The monitor interface of the base plate comprises a coupling part 210 for forming a mechanical connection, such as a releasable coupling between the monitor device and the base plate. The coupling part 210 is configured to engage with a coupling part of the monitor device for releasably coupling the monitor device to the base plate 4. Further, the monitor interface of the base plate 4 comprises a plurality of terminal elements respectively forming a plurality of terminals 212 for forming electrical connections with respective terminals of the monitor device. The coupling part 210 and the terminals 212 form a first connector 211 of the base plate 4. The base plate 4 comprises a first intermediate element 213 on the proximal side of the electrode assembly. The first intermediate element 213 is arranged between the terminal elements forming terminals 212 and the first adhesive layer (not shown). The first intermediate element 213 covers the terminal elements forming terminals 212 of the base plate 4 when seen in the axial direction and protects the first adhesive layer from mechanical stress from the terminal elements of the base plate.

As previously described, some parts of the illustrated base plate 4, may be provided as a separate assembly to be applied to an existing base plate, e.g. comprising one or more of the components as described, such as to provide a base plate like the base plate 4 as described. For example, a sensor assembly part 700 may be provided, e.g. comprising the electrode assembly 204, the first connector 211, the first intermediate element 213, the first adhesive layer 200 and the release liner 206. Additionally, the sensor assembly part 700 may also comprise the second adhesive layer 202 and/or the top layer 208. It may be envisioned that the user may provide a hole in layers of the base plate whereto the sensor assembly part 700 is to be applied, to allow for the first connector 211 of the sensor assembly part 700 to protrude through layers of the base plate whereto the sensor assembly part 700 is applied. Alternatively, the sensor assembly part 700 may be applied to the base plate such that the first connector 211 is positioned outside the periphery of the base plate.

Figure 4:
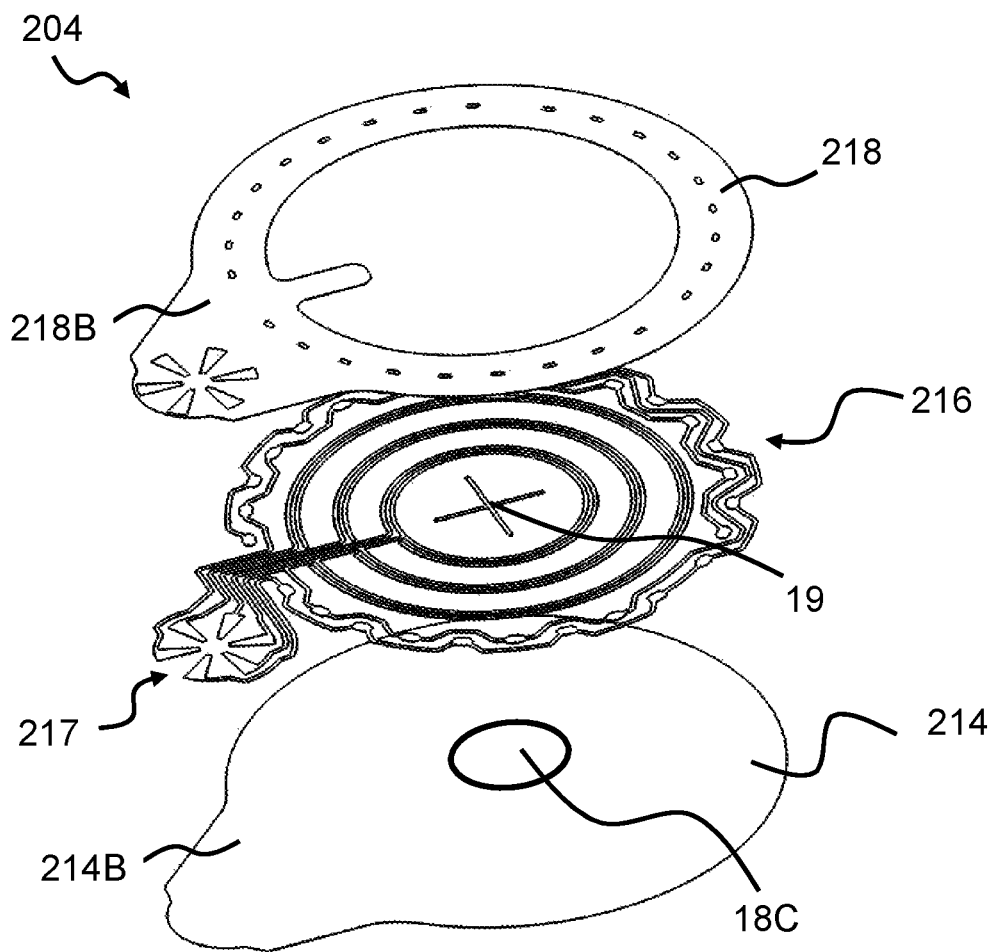
FIG. 4 is an exploded view of an exemplary electrode assembly.

FIG. 4 illustrates an exploded view of an exemplary electrode assembly 204 of a base plate and/or a sensor assembly part. The electrode assembly 204 has a distal side 204A and a proximal side 204B. The electrode assembly 204 comprises a support layer 214 with proximal surface 214B and electrodes 216 arranged on the proximal side of the support layer 214 and including a ground electrode, a first electrode, a second electrode, a third electrode, a fourth electrode, and a fifth electrode, wherein each electrode has a respective connection part 217 for connecting the electrodes 216 to respective terminal elements of the monitor interface. The electrodes 216 are positioned and/or formed on a proximal side 214B of the support layer 214. Further, electrode assembly 204 comprises a masking element 218 with proximal surface 218B and configured to insulate electrode parts of electrodes 216 from the first adhesive layer of the base plate and/or the sensor assembly part. The masking element 218 covers or overlap with parts of the electrodes 216 when seen in the axial direction.

Figure 5:
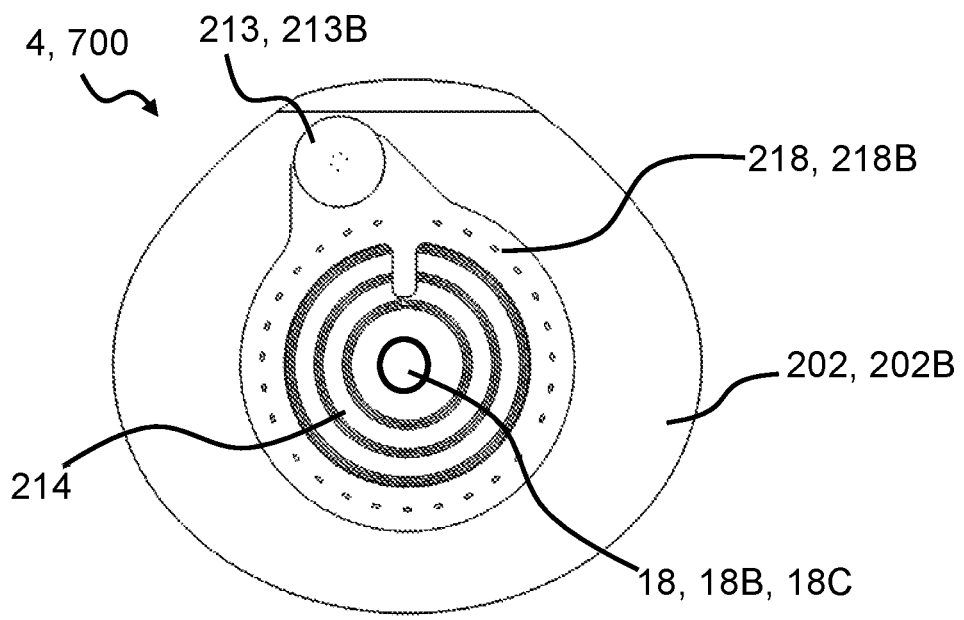
FIG. 5 is a proximal view of parts of a base plate and/or sensor assembly part.

FIG. 5 is a proximal view of proximal surfaces of base plate parts of the base plate and/or the sensor assembly part without the first adhesive layer and the release liner. The base plate 4 and/or the sensor assembly part 700 comprises a first intermediate element 213 on the proximal side of the electrode assembly, i.e. between the electrode assembly 204 and the first adhesive layer (not shown). The first intermediate element 213 covers the terminal elements of the base plate 4 when seen in the axial direction and protects the first adhesive layer from mechanical stress from the terminal elements of the base plate and/or the sensor assembly part.

Figure 6:
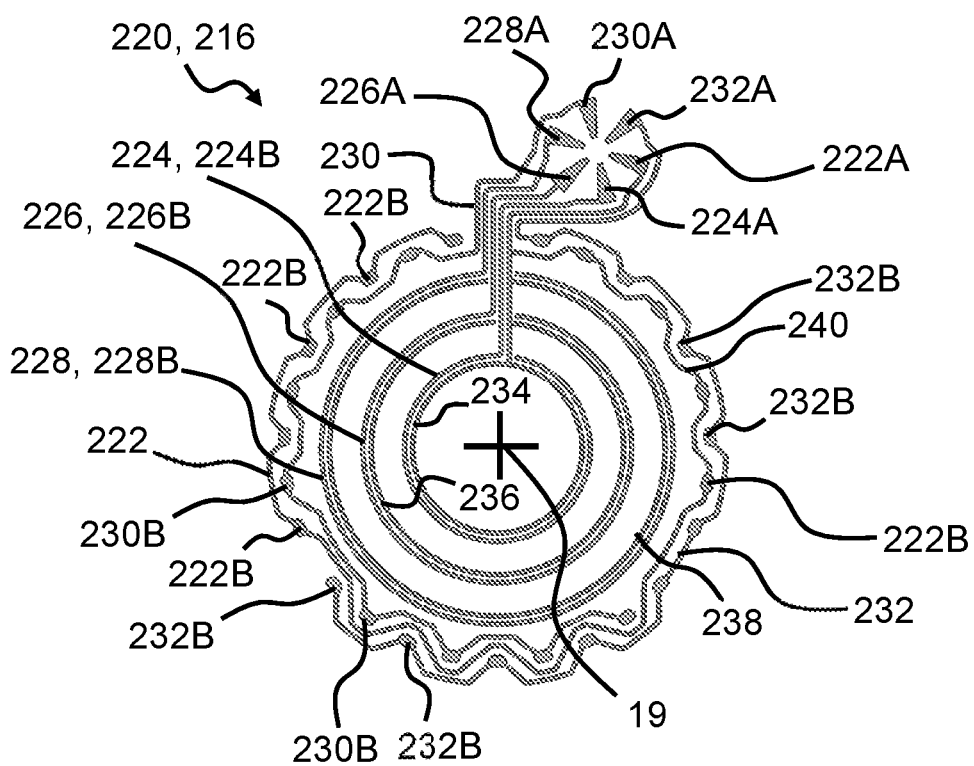
FIG. 6 is a distal view of an exemplary electrode configuration.

FIG. 6 is a distal view of an exemplary electrode configuration 220 of electrodes 216 of the electrode assembly 204. The electrode assembly 204, such as the electrode configuration 220 of the electrode assembly 204 comprises a ground electrode 222, a first electrode 224, a second electrode 226, a third electrode 228, a fourth electrode 230, and a fifth electrode 232. The ground electrode 222 comprises a ground connection part 222A and the first electrode 224 comprises a first connection part 224A. The second electrode 226 comprises a second connection part 226A and the third electrode 228 comprises a third connection part 228A. The fourth electrode 230 comprises a fourth connection part 230A and the fifth electrode 232 comprise a fifth connection part 232A.

The fourth electrode (second leakage electrode) 230 comprises fourth sensing parts 230B. The fifth electrode (third leakage electrode) 232 comprises fifth sensing parts 232B.

The ground electrode 222 comprises a first electrode part 234 for forming a ground or reference for the first electrode 224. The ground electrode 222 comprises a second electrode part 236 for forming a ground or reference for the second electrode 226. The ground electrode 222 comprises a third electrode part 238 for forming a ground or reference for the third electrode 228. The masking element 218 is arranged proximal to the electrodes 222, 224, 226, 228 covering and insulating parts of the electrodes from the first adhesive and forming respective conductor parts of the electrodes 222, 224, 226, 228. The parts of the electrodes 222, 224, 226, 228 not covered by the masking element 219 contacts the first adhesive layer and form sensing parts 224B, 226B, 228B of electrodes 224, 226, 228, respectively. Further, the electrode parts 234, 236, 238 form sensing parts of the ground electrode 222.

Figure 11:
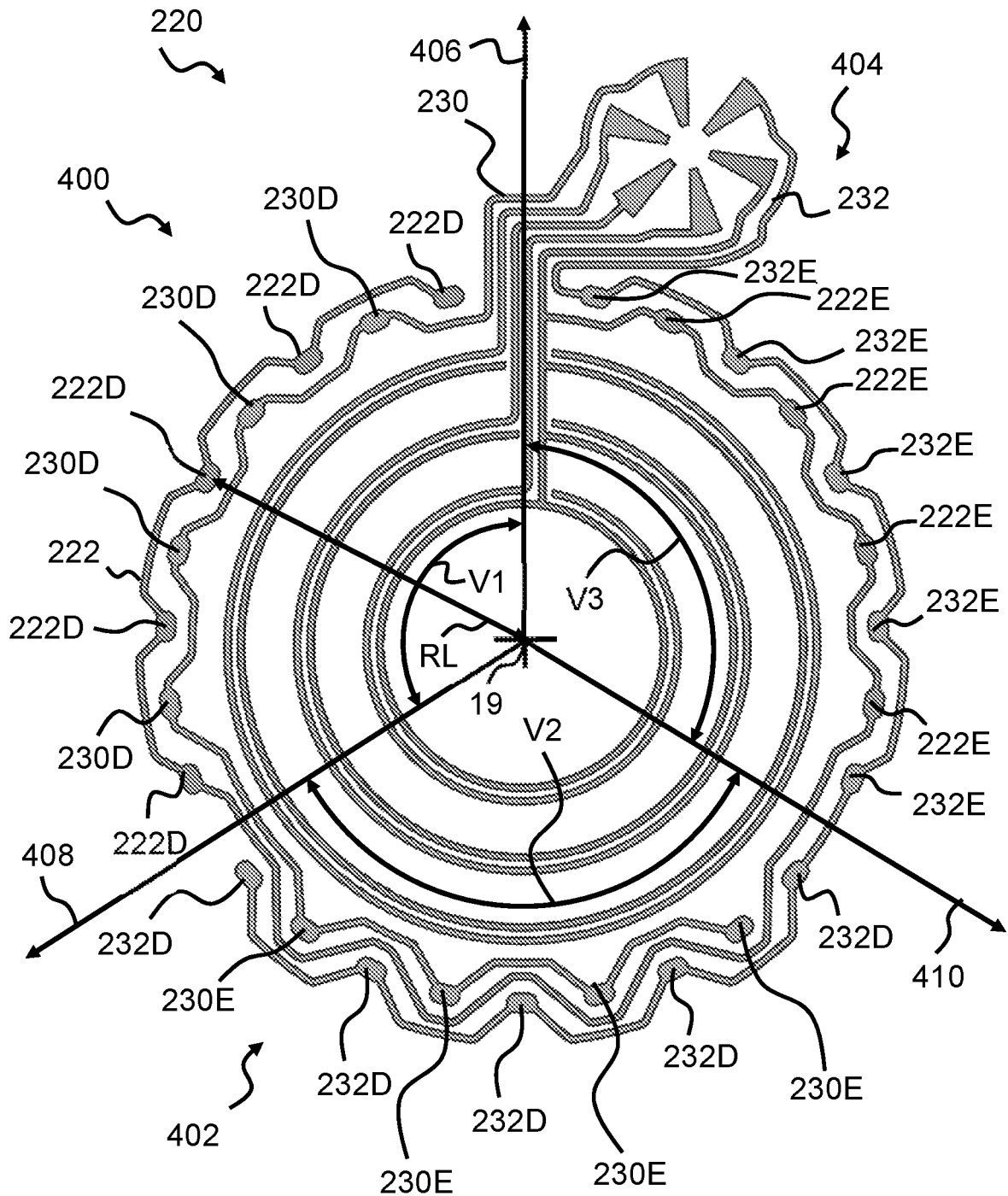
FIG. 11 is a distal view of the electrode configuration of FIG. 6.

The first sensing part 224B extends circularly at least 330 degrees around the stomal opening at a first radial distance R1 from the center point 19, see also FIG. 11. The first radial distance R1 is 14 mm. The first electrode part 234 is arranged on the inside of the first sensing part (i.e. closer to the center point) and extends circularly at least 330 degrees around the stomal opening at a first ground distance RG1 from the first sensing part (radially from the center point). The first ground distance RG1 is about 1 mm.

The second sensing part 226B extends circularly at least 330 degrees around the stomal opening at a second radial distance R2 from the center point 19, see also FIG. 11. The second radial distance R2 is 18 mm. The second electrode part 236 is arranged on the inside of the second sensing part 226B (i.e. closer to the center point) and extends circularly at least 330 degrees around the stomal opening at a second ground distance RG2 from the second sensing part 226B (radially from the center point). The second ground distance RG2 is about 1 mm.

The third sensing part 228B extends circularly at least 330 degrees around the stomal opening at a third radial distance R3 from the center point 19, see also FIG. 11. The third radial distance R3 is about 26 mm. The third electrode part 238 is arranged on the inside of the third sensing part 228B (i.e. closer to the center point) and extends circularly at least 330 degrees around the stomal opening at a third ground distance RG3 from the third sensing part 228B (radially from the center point). The third ground distance RG3 is about 1 mm.

The ground electrode 222 comprises a fourth electrode part 240 for forming a ground or reference for the fourth electrode 230 and the fifth electrode 232. The fourth electrode part 240 of the ground electrode forms the first leakage electrode. The fourth electrode part 240 of the ground electrode 222 extends at least 300 degrees around the stomal opening and comprises ground sensing parts 222B. The fourth sensing parts 230B, fifth sensing parts 232B, and ground sensing parts of the fourth electrode part 240 are circularly distributed around the center point 19 at a leakage radius from the center point. The fourth sensing parts 230B, fifth sensing parts 232B, and ground sensing parts of the fourth electrode part may have a radial extension larger than 1.0 mm, such as in the range from 1.5 mm to 3.0 mm, e.g. about 2.0 mm. The fourth sensing parts 230B, fifth sensing parts 232B, and ground sensing parts of the fourth electrode part 240 may have a circumferential extension (perpendicular to the radial extension) larger than 1.0 mm, such as in the range from 2.5 mm to 5.0 mm, e.g. about 3.5 mm. In one or more exemplary base plates and/or sensor assembly parts, the electrodes 224, 226, 228 and electrode parts 234, 236, 238 may be omitted from the electrode configuration/electrode assembly.

Figure 7:
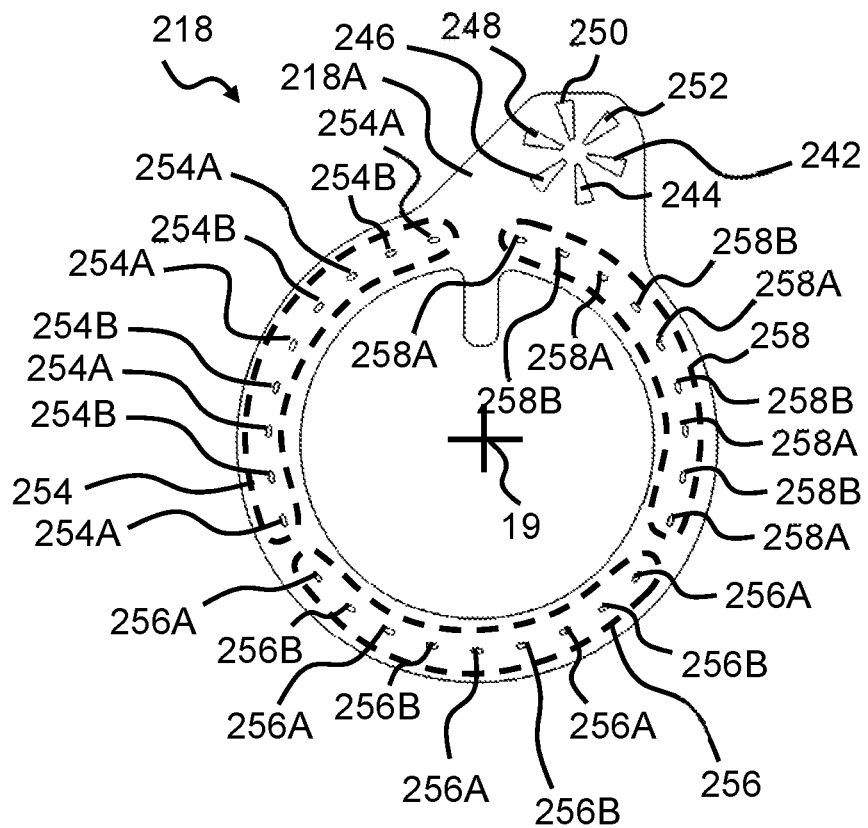
FIG. 7 is a distal view of an exemplary masking element.

FIG. 7 is a distal view of an exemplary masking element. The masking element 218 optionally has a plurality of terminal openings including six terminal openings. The plurality of terminal openings comprises a ground terminal opening 242, a first terminal opening 244, a second terminal opening 246, a third terminal opening 248, a fourth terminal opening 250, and a fifth terminal opening 252. The terminal openings 242, 244, 246, 248, 250, 252 of the masking element 218 are configured to overlap and/or be aligned with respective connection parts 222A, 224A, 226A, 228A, 230A, 232A of the electrodes of the electrode assembly.

The masking element 218 has a plurality of sensor point openings. The sensor point openings comprise primary sensor point openings shown within dotted line 254, each primary sensor point opening configured to overlap a part of the ground electrode (first leakage electrode) 222 and/or a part of the fourth electrode (second leakage electrode) 230. The primary sensor point openings 254 comprise, in the illustrated exemplary masking element, five primary sensor point openings 254A each configured to overlap a respective sensing part of the ground electrode (first leakage electrode) 222. The primary sensor point openings 254 comprise, in the illustrated exemplary masking element, four primary sensor point openings 254B each configured to overlap a respective sensing part of the fourth electrode (second leakage electrode) 230. The sensor point openings comprise secondary sensor point openings shown within dotted line 256, each second sensor point opening configured to overlap a part of the fourth electrode (second leakage electrode) 230 and/or a part of the fifth electrode (third leakage electrode) 232. The secondary sensor point openings 256 comprise, in the illustrated exemplary masking element, five secondary sensor point openings 256A each configured to overlap a respective sensing part of the fifth electrode (third leakage electrode) 232. The secondary sensor point openings 256 comprise, in the illustrated exemplary masking element, four secondary sensor point openings 256B each configured to overlap a respective sensing part of the fourth electrode (second leakage electrode) 230. The sensor point openings comprise tertiary sensor point openings shown within dotted line 258, each tertiary sensor opening configured to overlap a part of the fifth electrode (third leakage electrode) 232 and/or a part of the ground electrode (first leakage electrode) 222. The tertiary sensor point openings 258 comprise, in the illustrated exemplary masking element, five tertiary sensor point openings 258A each configured to overlap a respective sensing part of the fifth electrode (third leakage electrode) 232. The tertiary sensor point openings 258 comprise, in the illustrated exemplary masking element, four tertiary sensor point openings 258B each configured to overlap a respective sensing part of the ground electrode (first leakage electrode) 222. The sensor point openings 254A, 254B, 256A, 256B, 258A, 258B, are circularly arranged at a leakage radius of about 30 mm from the center point 19.

Figure 8:
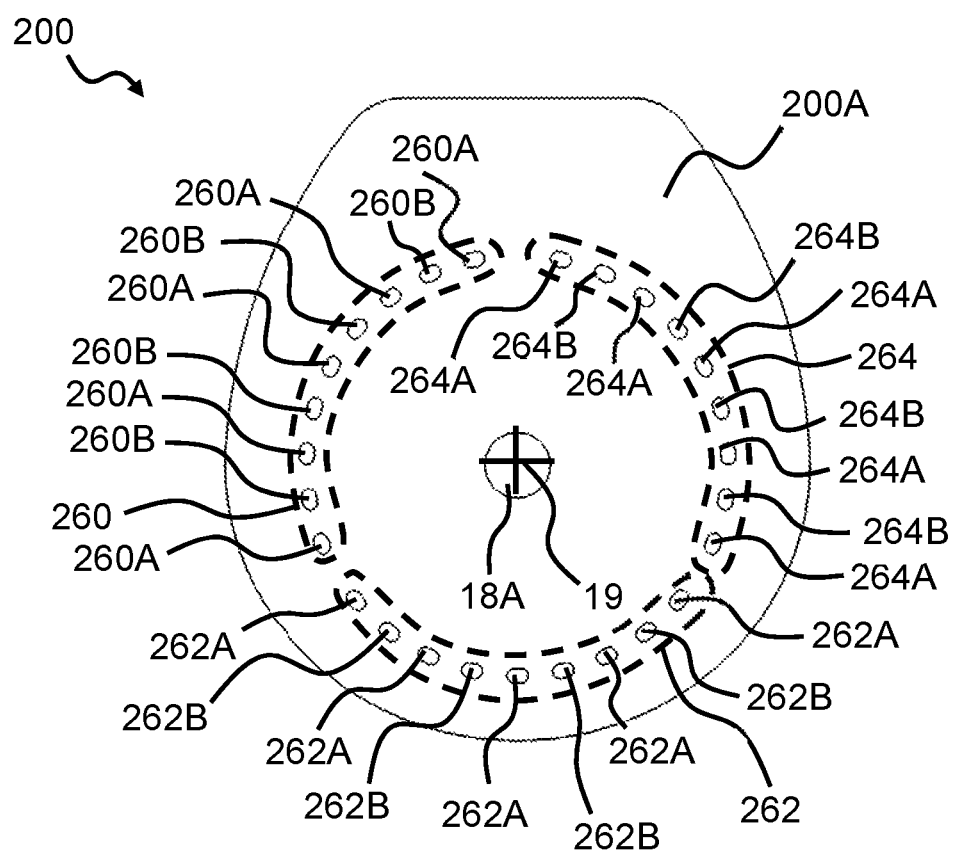
FIG. 8 is a distal view of an exemplary first adhesive layer.

FIG. 8 is a distal view of an exemplary first adhesive layer. The first adhesive layer 200 has a plurality of sensor point openings. The sensor point openings of the first adhesive layer comprise primary sensor point openings shown within dotted line 260, each primary sensor point opening configured to overlap a part of the ground electrode 222 and/or a part of the fourth electrode 230 of the electrode assembly. The primary sensor point openings comprise, in the illustrated exemplary first adhesive layer, five primary sensor point openings 260A each configured to overlap a respective sensing part of the ground electrode 222. The primary sensor point openings comprise, in the illustrated exemplary first adhesive layer, four primary sensor point openings 260B each configured to overlap a respective sensing part of the fourth electrode 230. The sensor point openings of the first adhesive layer comprise secondary sensor point openings shown within dotted line 262, each second sensor point opening configured to overlap a part of the fourth electrode 230 and/or a part of the fifth electrode 232 of the electrode assembly. The secondary sensor point openings comprise, in the illustrated exemplary first adhesive layer, five secondary sensor point openings 262A each configured to overlap a respective sensing part of the fifth electrode 232. The secondary sensor point openings comprise, in the illustrated exemplary first adhesive layer, four secondary sensor point openings 262B each configured to overlap a respective sensing part of the fourth electrode 230. The sensor point openings of the first adhesive layer comprise tertiary sensor point openings shown within dotted line 264, each tertiary sensor opening configured to overlap a part of the fifth electrode 232 and/or a part of the ground electrode 222 of the electrode assembly. The tertiary sensor point openings comprise, in the illustrated exemplary first adhesive layer, five tertiary sensor point openings 264A each configured to overlap a respective sensing part of the fifth electrode 232. The tertiary sensor point openings comprise, in the illustrated exemplary first adhesive layer, four tertiary sensor point openings 264B each configured to overlap a respective sensing part of the ground electrode 222.

Figure 9:
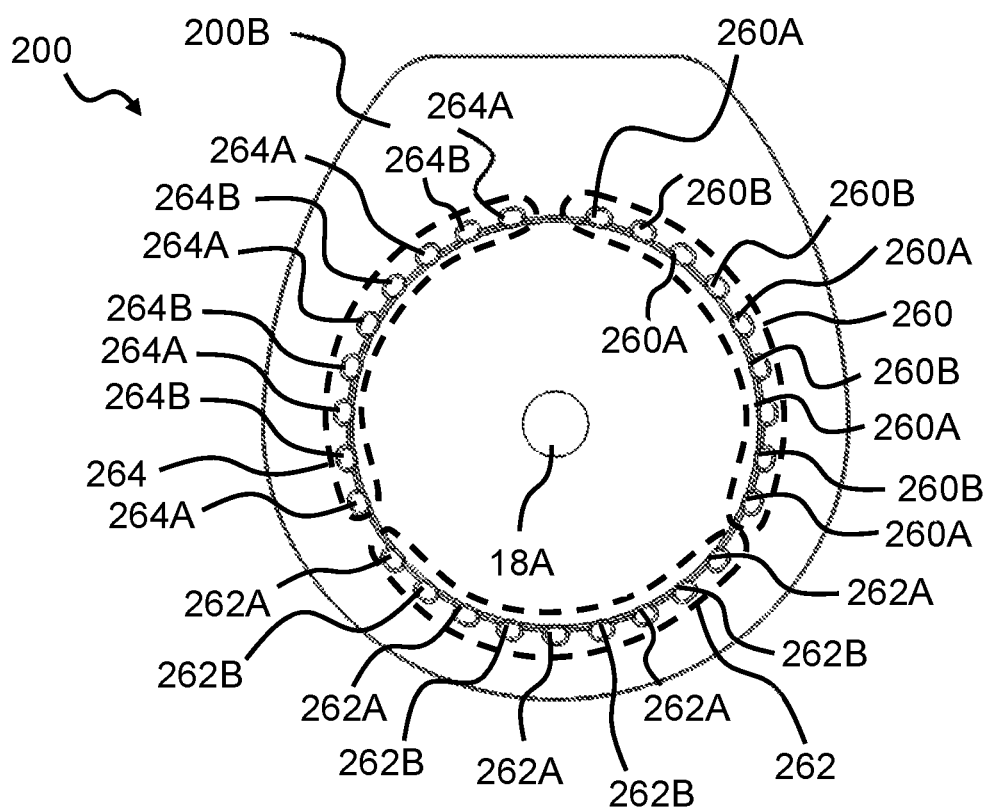
FIG. 9 is a proximal view of the first adhesive layer of FIG. 8.

FIG. 9 is a proximal view of the first adhesive layer of FIG. 8. The sensor point openings 260A, 260B, 262A, 262B, 264A, 264B, are circularly arranged at a leakage radius of about 30 mm from the center point.

Figure 10:
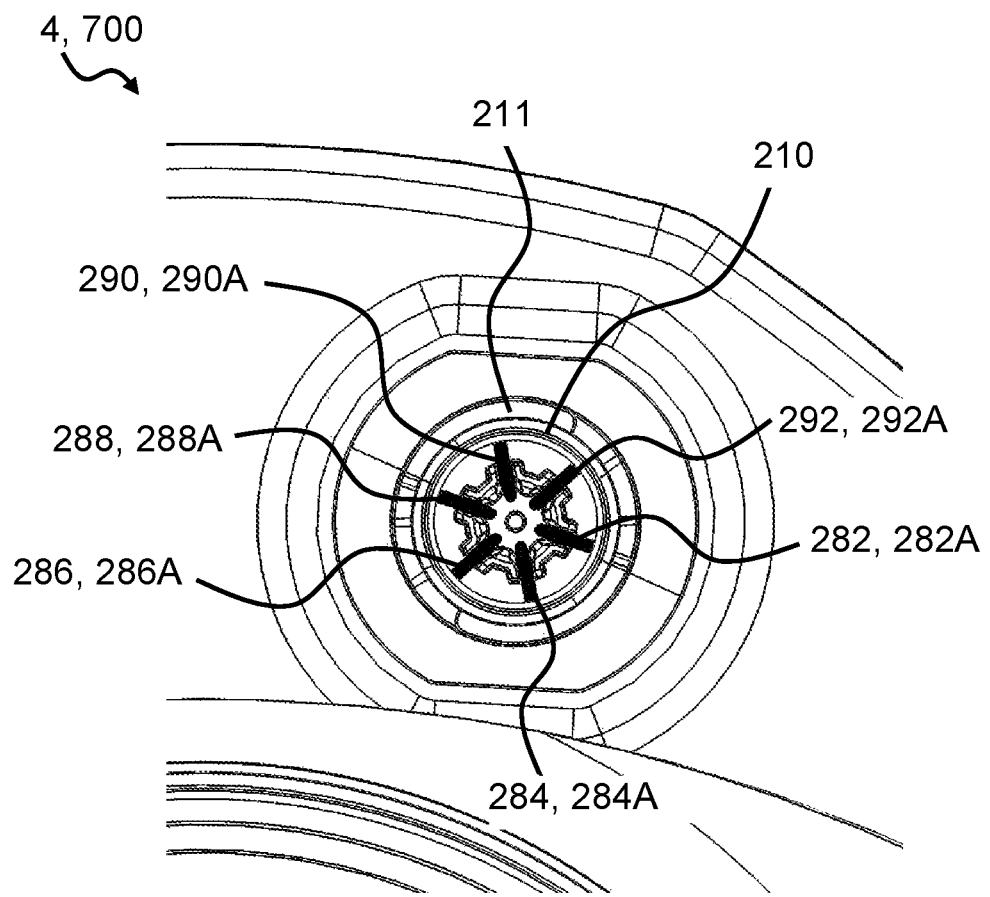
FIG. 10 is a distal view of a part of the base plate and/or sensor assembly part including a monitor interface.

FIG. 10 is a more detailed distal view of a part of the base plate 4 and/or the sensor assembly part 700. The base plate 4 and/or the sensor assembly part 700 comprises a monitor interface. The monitor interface comprises the first connector 211. The first connector 211 comprises coupling part 210 configured to releasably couple the monitor device to the base plate and/or the sensor assembly part and thus forming a releasable coupling. The first connector 211 of the monitor interface comprises a plurality of terminals formed by respective terminal elements for forming respective electrical connections with respective terminals of the monitor device.

The plurality of terminals of the first connector 211 of the monitor interface comprises a ground terminal element 282 forming a ground terminal 282A, a first terminal element 284 forming a first terminal 284, a second terminal element 286 forming a second terminal 286A, and optionally a third terminal element 288 forming a third terminal 288A. The monitor interface optionally comprises a fourth terminal element 290 forming a fourth terminal 290A and/or a fifth terminal element 292 forming a fifth terminal 292A. The terminal elements 282, 284, 286, 288, 290, 292 contact respective connection parts 222A, 224A, 226A, 228A, 230a, 232A of electrodes 222, 224, 226, 228, 230, 232.

The position of the first connector on the base plate and/or the sensor assembly part, the number of terminals and the position of the terminals in the coupling part may be adapted to the electrode configuration used in the electrode assembly of the base plate and/or the sensor assembly part. For example, a first connector for a base plate and/or a sensor assembly part with the electrode configuration 220A shown in FIG. 11 comprises four terminals respectively connected to connection parts 222A, 224A, 226A, 228A of the electrodes, and a first connector for a base and/or a sensor assembly part plate with the electrode configuration 220B shown in FIG. 12 comprises three terminals respectively connected to connection parts 222A, 224A, 226A of the electrodes.

FIG. 11 is a distal view of the exemplary electrode configuration 220 of FIG. 6 for a base plate and/or a sensor assembly part. The electrode configuration 220 comprises a first leakage electrode 222, second leakage electrode 230, and third leakage electrode 232. The leakage electrodes 222, 230, 232 are configured to detect presence of fluid on the proximal side of the first adhesive layer in three sensing zones (three angular sensing zones, in the illustrated example), primary sensing zone 400, secondary sensing zone 402, and tertiary sensing zone 404. The primary sensing zone 400 is arranged in a primary angle space between a first direction 406 and a second direction 408 from the center point 19, wherein the primary angle space spans a primary angle V1 of 120°. The secondary sensing zone 402 is arranged in a secondary angle space between the second direction 408 and a third direction 410 from the center point 19, wherein the secondary angle space spans a secondary angle V2 of 120°. The tertiary sensing zone 404 is arranged in a tertiary angle space between the third direction 410 and the first direction 406 from the center point 19, wherein the tertiary angle space spans a tertiary angle V3 of 120°.

The first leakage electrode 222 comprises five primary sensing parts 222D arranged in the primary sensing zone 400, and four tertiary sensing parts 222E arranged in the tertiary sensing zone 404. Each primary sensing part 222D is aligned with a respective primary sensor point opening 254A of the masking element 218 (see FIG. 7). Further, each primary sensing part 222D is aligned with a respective primary sensor point opening 260A of the first adhesive layer 200 (see FIG. 8). Each tertiary sensing part 222E of the first leakage electrode 222 is aligned with a respective tertiary sensor point opening 258B of the masking element 218 (see FIG. 7). Further, each tertiary first sensing part 222E is aligned with a respective tertiary sensor point opening 264B of the first adhesive layer 200 (see FIG. 8).

The second leakage electrode 230 comprises four primary sensing parts 230D arranged in the primary sensing zone 400, and four secondary sensing parts 230E arranged in the secondary sensing zone 402. Each primary sensing part 230D is aligned with a respective primary sensor point opening 254B of the masking element 218 (see FIG. 7). Further, each primary sensing part 230D is aligned with a respective primary sensor point opening 260B of the first adhesive layer 200 (see FIG. 8). Each secondary sensing part 230E is aligned with a respective secondary sensor point opening 256B of the masking element 218 (see FIG. 7). Further, each secondary sensing part 230E is aligned with a respective secondary sensor point opening 262B of the first adhesive layer 200 (see FIG. 8).

The third leakage electrode 232 comprises five secondary sensing parts 232D arranged in the secondary sensing zone 402, and five tertiary sensing parts 232E arranged in the tertiary sensing zone 404. Each secondary sensing part 232D is aligned with a respective secondary sensor point opening 256A of the masking element 218 (see FIG. 7). Further, each secondary sensing part 232D is aligned with a respective secondary sensor point opening 262A of the first adhesive layer 200 (see FIG. 8). Each tertiary sensing part 232E is aligned with a respective tertiary sensor point opening 258A of the masking element 218 (see FIG. 7). Further, each tertiary sensing part 232E is aligned with a respective tertiary sensor point opening 264A of the first adhesive layer 200 (see FIG. 8). The sensing parts 222D, 222E, 230D, 230E, 232D, 232E are circularly arranged at a leakage radius RL of about 30 mm from the center point.

Figure 12:
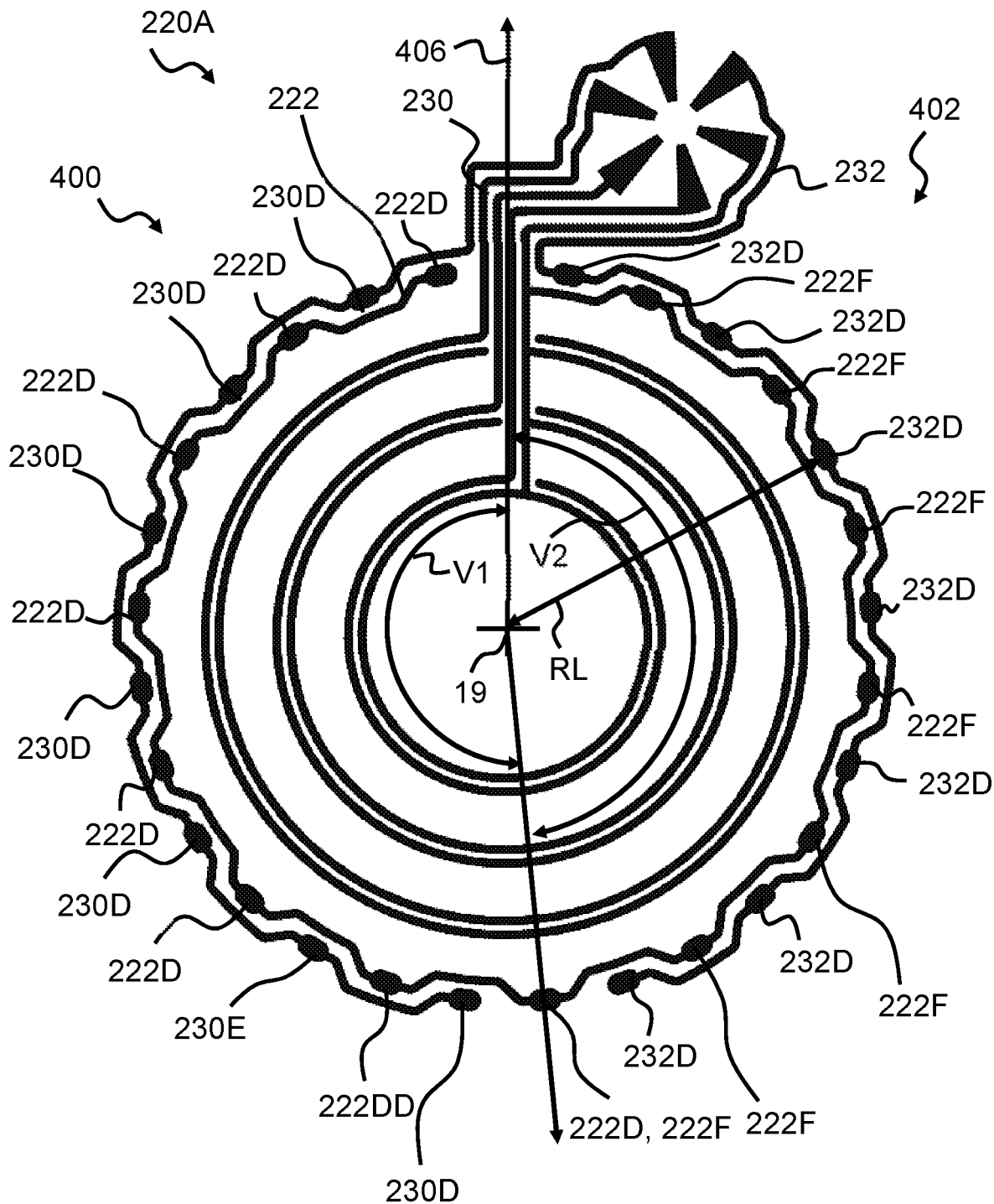
FIG. 12 is a distal view of an exemplary electrode configuration.

FIG. 12 is a distal view of an exemplary electrode configuration 220A for a base plate and/or a sensor assembly part. The electrode configuration 220 comprises a first leakage electrode 222, second leakage electrode 230, and third leakage electrode 232. The leakage electrodes 222, 230, 232 are configured to detect presence of fluid on the proximal side of the first adhesive layer in two angular sensing zones, primary sensing zone 400 and secondary sensing zone 402. The primary sensing zone 400 is arranged in a primary angle space between a first direction 406 and a second direction 408 from the center point 19, wherein the primary angle space spans a primary angle V1 of about 185°. The secondary sensing zone 402 is arranged in a secondary angle space between the second direction 408 and the first direction 406 from the center point 19, wherein the secondary angle space spans a secondary angle V2 of about 175°.

The first leakage electrode 222 comprises primary sensing parts 222D arranged in the primary sensing zone 400, and secondary sensing parts 222F arranged in the secondary sensing zone 402. The second leakage electrode 230 comprises primary sensing parts 230D arranged in the primary sensing zone 400. The third leakage electrode 232 comprises secondary sensing parts 232D arranged in the secondary sensing zone 402. Each primary sensing part 222D, 230D is aligned with a respective primary sensor point opening of the masking element 219 (see FIG. 13) and with a respective primary sensor point opening of the first adhesive layer 201 (see FIG. 14). The sensing parts 222D, 222F, 230D, and 232D are circularly arranged at a leakage radius RL of about 30 mm from the center point.

Figure 13:
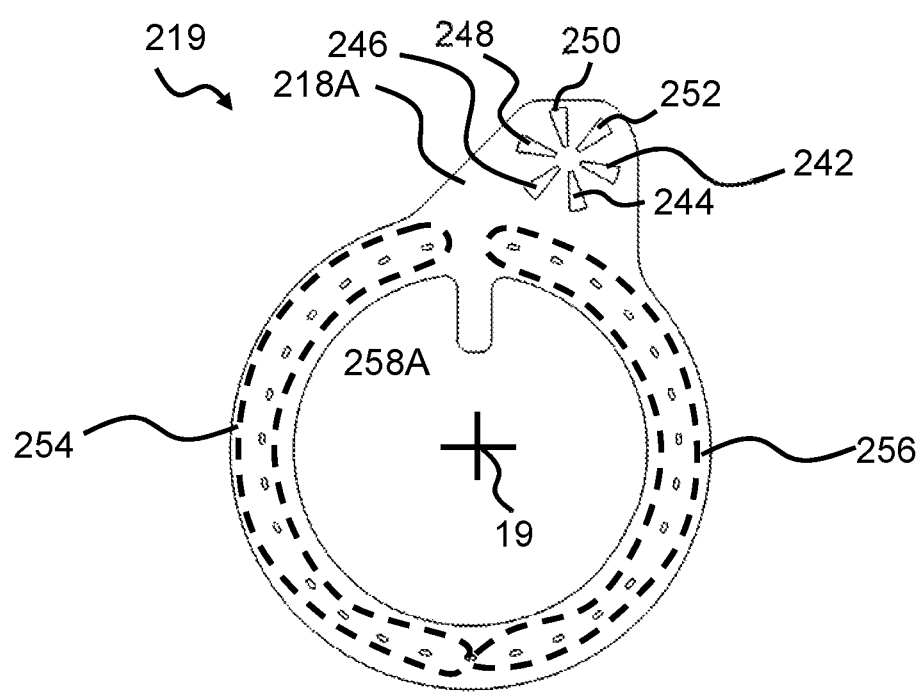
FIG. 13 is a distal view of an exemplary masking element.
Figure 14:
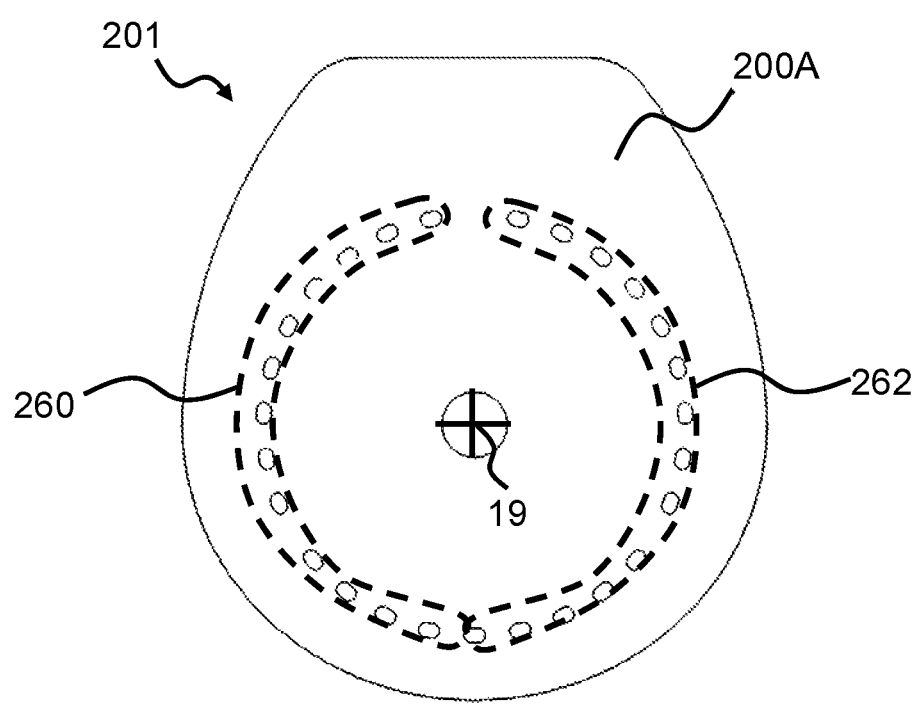
FIG. 14 is a distal view of an exemplary first adhesive layer.

FIG. 13 is a distal view of masking layer 219 for electrode configuration 220A in FIG. 12. The masking layer 219 comprises primary sensor point openings 254 and secondary sensor point openings 256. FIG. 14 is a distal view of first adhesive layer 201 for electrode configuration 220A in FIG. 12 implementing a base plate and/or a sensor assembly part with two sensing zones arranged in separate angle spaces. The masking layer 201 comprises primary sensor point openings 260 and secondary sensor point openings 262.

Figure 15:
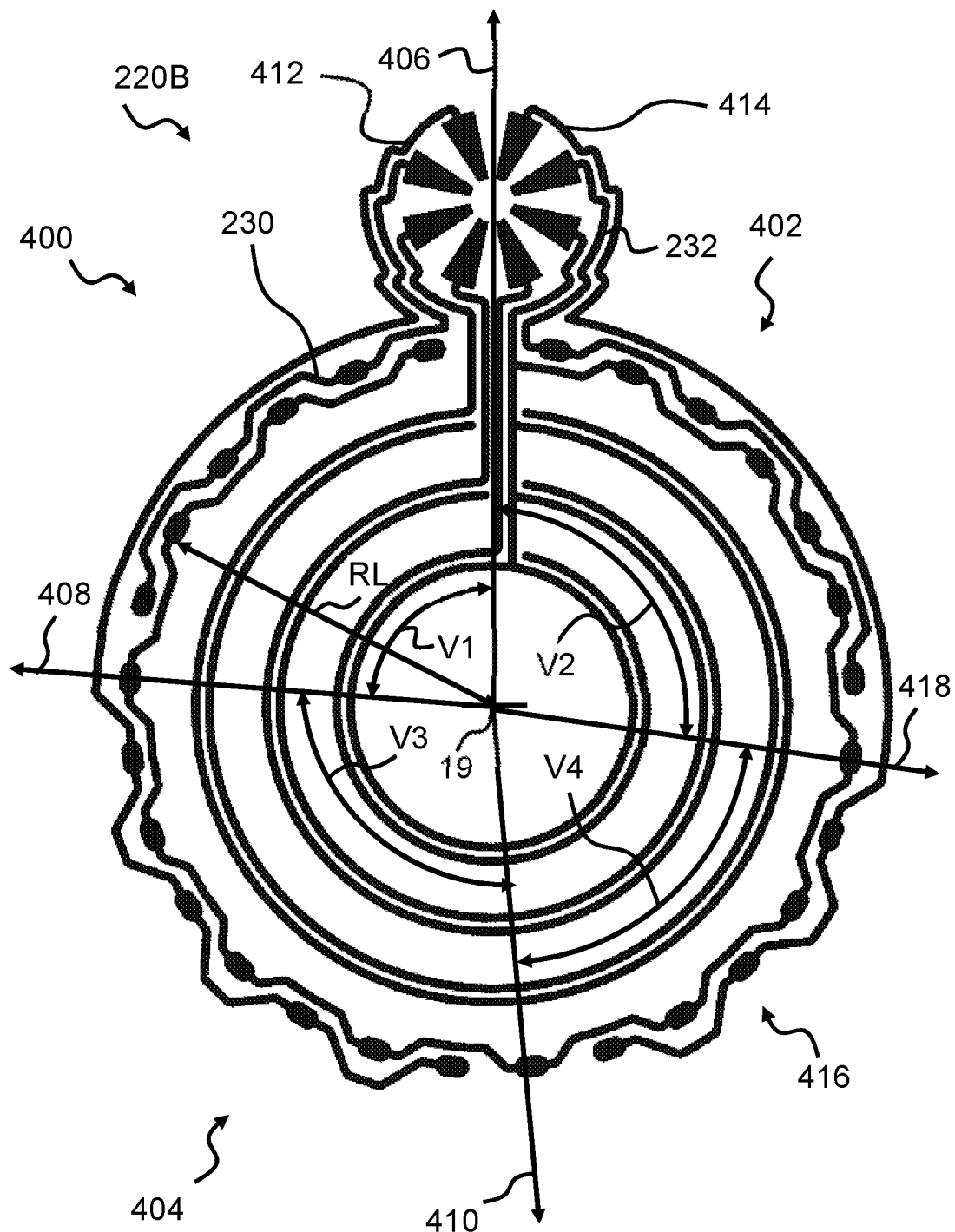
FIG. 15 is a distal view of an exemplary electrode configuration.

FIG. 15 is a distal view of an exemplary electrode configuration 220B for a base plate and/or the sensor assembly part. The electrode configuration 220B comprises first leakage electrode 222, second leakage electrode 230, third leakage electrode 232, fourth leakage electrode 412, and fifth leakage electrode 414. The leakage electrodes 222, 230, 232, 412, 414 are configured to detect presence of fluid on the proximal side of the first adhesive layer in four angular sensing zones 400, 402, 404, 416. The primary sensing zone 400 is arranged in a primary angle space spanning a primary angle V1 of about 85°. The secondary sensing zone 402 is arranged in a secondary angle space spanning a secondary angle V2 of about 95°. The tertiary sensing zone 404 is arranged in a tertiary angle space spanning a tertiary angle V3 of about 95°. The quaternary sensing zone 416 is arranged in a quaternary angle space spanning a quaternary angle V4 of about 85°.

While exemplary base plates and/or sensor assembly parts with two, three and four sensing zones have been described in more detail, the base plate and/or the sensor assembly part may comprise one or a larger number of sensing zones, such as five, six, seven, eight or more sensing zones.

Figure 16:
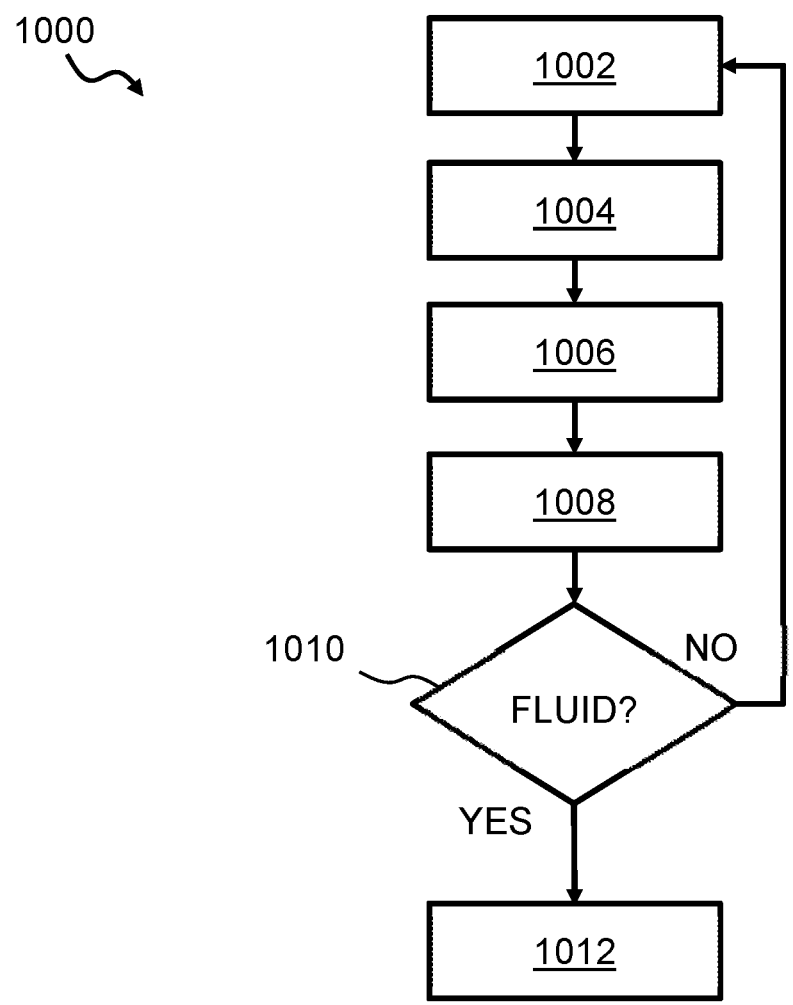
FIG. 16 is a flow diagram of an exemplary method.

FIG. 16 is a flow diagram of an exemplary method of monitoring a base plate and/or a sensor assembly part of an ostomy appliance, the base plate and/or the sensor assembly part comprising a first adhesive layer and a plurality of electrodes, the first adhesive layer having a proximal side configured for attachment of the base plate and/or the sensor assembly part to the skin surface of a user and a stomal opening with a center point, the plurality of electrodes including a first leakage electrode, a second leakage electrode, and a third leakage electrode. The method 1000 comprises obtaining 1002 a primary sensor signal (primary leakage ostomy data) from the first leakage electrode and the second leakage electrode; detecting 1004 presence of fluid on the proximal side in a primary sensing zone based on the primary sensor signal (primary leakage ostomy data); obtaining 1006 a secondary sensor signal (secondary leakage ostomy data) from the second leakage electrode and the third leakage electrode; detecting 1008 presence of fluid on the proximal side in a secondary sensing zone based on the secondary sensor signal (secondary leakage ostomy data); and in accordance 1010 with detection of presence of fluid in the primary sensing zone and/or the secondary sensing zone, providing 1012 a leakage indicator, e.g. a wireless monitor signal to an accessory device from a monitor device, indicative of the sensing zone in which presence of liquid has been detected. If no fluid is detected, the method returns to obtaining 1002 a primary sensor signal (primary leakage ostomy data) from the first leakage electrode and the second leakage electrode.

The method 1000 comprises obtaining 1002 a primary sensor signal (primary leakage ostomy data) from the first leakage electrode and the second leakage electrode; detecting 1004 presence of fluid on the proximal side in a primary sensing zone based on the primary sensor signal (primary leakage ostomy data); obtaining 1006 a secondary sensor signal (secondary leakage ostomy data) from the second leakage electrode and the third leakage electrode; detecting 1008 presence of fluid on the proximal side in a secondary sensing zone based on the secondary sensor signal (secondary leakage ostomy data); and in accordance 1010 with detection of presence of fluid in the primary sensing zone and/or the secondary sensing zone, providing 1012 a leakage indicator, e.g. a wireless monitor signal to an accessory device from a monitor device, indicative of the sensing zone in which presence of liquid has been detected. If no fluid is detected, the method returns to obtaining 1002 a primary sensor signal (primary leakage ostomy data) from the first leakage electrode and the second leakage electrode.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering. Furthermore, the labelling of a first element does not imply the presence of a second element and vice versa.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

Embodiments of the present disclosure are set out in the following items:

1. A sensor assembly part for an ostomy appliance, the sensor assembly part comprising:
   a first adhesive layer with a proximal side configured for attachment of the sensor assembly part to the skin surface of a user, the first adhesive layer having a stomal opening with a center point; and
   a plurality of electrodes including a first leakage electrode, a second leakage electrode, and a third leakage electrode, wherein the plurality of electrodes is configured to detect presence of fluid on the proximal side of the first adhesive layer in a primary sensing zone and a secondary sensing zone, the primary sensing zone arranged in a primary angle space from the center point of the first adhesive layer and the secondary sensing zone arranged in a secondary angle space from the center point of the first adhesive layer.

2. Sensor assembly part according to item 1, wherein the primary angle space spans a primary angle in the range from 45° to 315°.

3. Sensor assembly part according to any of items 1-2, wherein the secondary angle space spans a secondary angle in the range from 45° to 315°.

4. Sensor assembly part according to any of items 1-3, wherein the primary sensing zone and the secondary sensing zone are separate sensing zones.

5. Sensor assembly part according to any of items 1-4, wherein the first leakage electrode comprises one or more primary first sensing parts arranged in the primary sensing zone.

6. Sensor assembly part according to any of items 1-5, wherein the second leakage electrode comprises one or more primary second sensing parts arranged in the primary sensing zone.

7. Sensor assembly part according to any of items 1-6, wherein the second leakage electrode comprises one or more secondary second sensing parts arranged in the secondary sensing zone.

8. Sensor assembly part according to any of items 1-7, wherein the third leakage electrode comprises one or more secondary third sensing parts arranged in the secondary sensing zone.

9. Sensor assembly part according to any of items 1-8, wherein the plurality of electrodes is configured to detect presence of fluid on the proximal side in a tertiary sensing zone, the tertiary sensing zone arranged in a tertiary angle space from the center point of the first adhesive layer.

10. Sensor assembly part according to item 9, wherein the tertiary angle space spans a tertiary angle in the range from 45° to 180°.

11. Sensor assembly part according to any of items 9-10, wherein the primary sensing zone and the tertiary sensing zone are separate sensing zones.

12. Sensor assembly part according to any of items 9-11, wherein the first leakage electrode comprises one or more tertiary first sensing parts arranged in the tertiary sensing zone.

13. Sensor assembly part according to any of items 9-12, wherein the third leakage electrode comprises one or more tertiary third sensing parts arranged in the tertiary sensing zone.

14. A method of monitoring a sensor assembly part of an ostomy appliance, the sensor assembly part comprising a first adhesive layer and a plurality of electrodes, the first adhesive layer having a proximal side configured for attachment of the sensor assembly part to the skin surface of a user and a stomal opening with a center point, the plurality of electrodes including a first leakage electrode, a second leakage electrode, and a third leakage electrode, the method comprising:
obtaining a primary sensor signal from the first leakage electrode and the second leakage electrode;
detecting presence of fluid on the proximal side in a primary sensing zone based on the primary sensor signal; obtaining a secondary sensor signal from the second leakage electrode and the third leakage electrode;
detecting presence of fluid on the proximal side in a secondary sensing zone based on the secondary sensor signal; and
in accordance with detection of presence of fluid in the primary sensing zone and/or the secondary sensing zone, providing a leakage indicator indicative of the sensing zone in which presence of liquid has been detected.

15. A monitor device for an ostomy system comprising an ostomy appliance with a base plate having a first adhesive layer with a proximal side configured for attachment of the base plate to the skin surface of a user, the first adhesive layer having a stomal opening with a center point, the monitor device comprising:
a processor;
memory;
a first interface connected to the processor and the memory, the first interface configured for obtaining ostomy data from the base plate coupled to the first interface, the ostomy data comprising primary leakage ostomy data from a primary electrode set of the base plate and secondary leakage ostomy data from a secondary electrode set of the base plate; and
a second interface connected to the processor,
wherein the processor is configured to:
obtain primary leakage parameter data based on the primary leakage ostomy data;
obtain secondary leakage parameter data based on the secondary leakage ostomy data;
detect presence of fluid on the proximal side of the first adhesive layer in a primary sensing zone based on the primary leakage parameter data, the primary sensing zone arranged in a primary angle space from the center point of the first adhesive layer;
detect presence of fluid on the proximal side of the first adhesive layer in a secondary sensing zone based on the secondary leakage parameter data, the secondary sensing zone arranged in a secondary angle space from the center point of the first adhesive layer;
in accordance with a detection of presence of fluid in the primary sensing zone, transmit a primary leakage monitor signal comprising monitor data indicative of presence of fluid in the primary sensing zone via the second interface; and
in accordance with a detection of presence of fluid in the secondary sensing zone, transmit a secondary leakage monitor signal comprising monitor data indicative of presence of fluid in the secondary sensing zone via the second interface.

16. Monitor device according to item 15, wherein the ostomy data comprises tertiary leakage ostomy data from a tertiary electrode set of the base plate, wherein the processor is configured to:
obtain tertiary leakage parameter data based on the primary leakage ostomy data;
detect presence of fluid on the proximal side of the first adhesive layer in a tertiary sensing zone based on the tertiary leakage parameter data, the tertiary sensing zone arranged in a tertiary angle space from the center point of the first adhesive layer; and
in accordance with a detection of presence of fluid in the tertiary sensing zone, transmit a tertiary leakage monitor signal comprising monitor data indicative of presence of fluid in the tertiary sensing zone via the second interface.

17. Monitor device according to any of items 15-16, wherein to detect presence of fluid on the proximal side of the first adhesive layer in a primary sensing zone is based on a primary leakage criteria set based on the primary leakage parameter data, wherein fluid is present in the primary sensing zone if the primary leakage criteria set is satisfied.

18. Monitor device according to item 17, wherein the primary leakage criteria set is based on a primary leakage threshold value stored in the memory.

19. Monitor device according to any of items 15-18, wherein to detect presence of fluid on the proximal side of the first adhesive layer in a secondary sensing zone is based on a secondary leakage criteria set based on the secondary leakage parameter data, wherein fluid is present in the secondary sensing zone if the secondary leakage criteria set is satisfied.

20. Monitor device according to item 19, wherein the secondary leakage criteria set is based on a secondary leakage threshold value stored in the memory.

21. Monitor device according to any of items 15-20 as dependent on item 16, wherein to detect presence of fluid on the proximal side of the first adhesive layer in a tertiary sensing zone is based on a tertiary leakage criteria set based on the tertiary leakage parameter data, wherein fluid is present in the tertiary sensing zone if the tertiary leakage criteria set is satisfied.

22. Monitor device according to item 21, wherein the tertiary leakage criteria set is based on a tertiary leakage threshold value stored in the memory.

23. Monitor device according to any of items 15-22, wherein the second interface comprises a loudspeaker connected to the processor, and wherein the processor is configured to transmit a monitor signal via the loudspeaker.

24. Monitor device according to any of items 15-23, wherein the second interface comprises an antenna and a wireless transceiver, and wherein the processor is configured to transmit a monitor signal as a wireless monitor signal via the antenna and the wireless transceiver.

25. An ostomy system comprising an ostomy appliance and a monitor device, the ostomy appliance comprising a base plate, wherein the monitor device is a monitor device according to any of items 15-24.

LIST OF REFERENCES 1 ostomy system
2 ostomy appliance
4 base plate
6 monitor device
8 accessory device
10 server device
12 network
14 coupling member
16 coupling ring
18, 18A, 18B, 18C, 18D stomal opening
20 docking station
22 first connector
24 user interface
100 monitor device housing
101 processor
102 first interface
104 second interface
106 memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver
126 loudspeaker
128 haptic feedback element
140 sensor unit
200, 201 first adhesive layer
200A distal surface of first adhesive layer
200B proximal surface of first adhesive layer
202 second adhesive layer
202A distal surface of second adhesive layer
202B proximal surface of second adhesive layer
204 electrode assembly
204A distal surface of electrode assembly
204B proximal surface of electrode assembly
206 release liner
206A distal surface of the release liner
206B proximal surface of the release liner
208 top layer
208A distal surface of the top layer
208B proximal surface of the top layer
209 coupling ring
210 coupling part of first connector
211 first connector
212 terminals of first connector
213 first intermediate element
213A distal surface of first intermediate element
213B proximal surface of first intermediate element
214 support layer of electrode assembly
214A distal surface of support layer
214B proximal surface of support layer
216 electrodes of electrode assembly
217 connection parts of electrodes
218, 219 masking element
218A distal surface of masking element
218B proximal surface of masking element
220, 220A, 220B electrode configuration
222 ground electrode, first leakage electrode
222A ground connection part
222B ground sensing part, sensing part of first leakage electrode
222C ground connector part
222D primary sensing part
222E tertiary sensing part
222F secondary sensing part
224 first electrode
224A first connection part
224B first sensing part
224C first conductor part
226 second electrode
226A second connection part
226B second sensing part
226C second conductor part
228 third electrode
228A third connection part
228B third sensing part
228C third conductor part
230 fourth electrode, second leakage electrode
230A fourth connection part
230B fourth sensing part, sensing part of second leakage electrode 230D primary sensing part
230E secondary sensing part
232 fifth electrode, third leakage electrode
232A fifth connection part
232B fifth sensing part, sensing part of third leakage electrode
232D secondary sensing part
232E tertiary sensing part
234 first electrode part of the ground electrode
236 second electrode part of the ground electrode
238 third electrode part of the ground electrode
240 fourth electrode part of the ground electrode
242 ground terminal opening
244 first terminal opening
246 second terminal opening
248 third terminal opening
250 fourth terminal opening
252 fifth terminal opening
254 primary sensor point openings of masking element
254A primary sensor point opening for the ground electrode (first leakage electrode)
254B primary sensor point opening for the fourth electrode (second leakage electrode)
256 secondary sensor point openings of masking element
256A secondary sensor point opening for the fifth electrode (third leakage electrode)
256B secondary sensor point opening for the fourth electrode (second leakage electrode)
258 tertiary sensor point openings of masking element
258B tertiary sensor point opening for the fifth electrode (third leakage electrode)
258A tertiary sensor point opening for the ground electrode (first leakage electrode)
260 primary sensor point openings of first adhesive layer
260A primary sensor point opening for the ground electrode (first leakage electrode)
260B primary sensor point opening for the fourth electrode (second leakage electrode)
262 secondary sensor point openings of first adhesive layer
262A secondary sensor point opening for the fifth electrode (third leakage electrode)
262B secondary sensor point opening for the fourth electrode (second leakage electrode)
264 tertiary sensor point openings of first adhesive layer
264A tertiary sensor point opening for the fifth electrode (third leakage electrode)
264B tertiary sensor point opening for the ground electrode (first leakage electrode)
282 ground terminal element
282A ground terminal
284 first terminal element
284A first terminal
286 second terminal element
286A second terminal
288 third terminal element
288A third terminal
290 fourth terminal element
290A fourth terminal
292 fifth terminal element
292A fifth terminal
400 primary sensing zone
402 secondary sensing zone
404 tertiary sensing zone
406 first direction/zero direction
408 second direction
410 third direction
412 fourth leakage electrode
414 fifth leakage electrode
416 quaternary sensing zone
418 fourth direction
700 sensor assembly part
1000 method of monitoring a base plate and/or a sensor assembly part of an ostomy appliance
1002 obtaining a primary sensor signal
1004 detecting presence of fluid in a primary sensing zone
1006 obtaining a secondary sensor signal
1008 detecting presence of fluid in a secondary sensing zone
1010 presence of fluid detected
1012 providing a leakage indicator
R1 first radial distance
RG1 first ground distance
R2 second radial distance
RG2 second ground distance
R3 third radial distance
RG3 third ground distance
RL leakage radius
V1 primary angle
V2 secondary angle
V3 tertiary angle
V4 tertiary angle

The invention claimed is:

1. A base plate for an ostomy appliance, the base plate comprising:
   a first adhesive layer with a proximal side configured for attachment of the base plate to the skin surface of a user, the first adhesive layer having a stomal opening with a center point;
   a primary angular sensing zone between a first direction and a second direction from the center point, the primary sensing zone having a first leakage electrode of a plurality of electrodes to enable detection of liquid between the first direction and the second direction; and
   a secondary angular sensing zone separate from the primary angular sensing zone and between the second direction and a third direction from the center point, the secondary sensing zone having a second leakage electrode of the plurality of electrodes to enable detection of liquid between the second direction and the third direction.

2. The base plate according to claim 1, wherein the primary angular sensing zone spans a primary angle in the range from 45° to 315°.

3. The base plate according to claim 1, wherein the secondary angular sensing zone spans a secondary angle in the range from 45° to 315°.

4. The base plate according to claim 1, further comprising a third leakage electrode in the primary angular sensing zone and the secondary angular sensing zone.

5. The base plate according to claim 1, wherein the first leakage electrode comprises one or more primary first sensing parts arranged in the primary angular sensing zone.

6. The base plate according to claim 4, wherein the third leakage electrode comprises one or more primary second sensing parts arranged in the primary angular sensing zone.

7. The base plate according to claim 1, wherein the second leakage electrode comprises one or more secondary second sensing parts arranged in the secondary angular sensing zone.

8. The base plate according to claim 4, wherein the third leakage electrode comprises one or more secondary third sensing parts arranged in the secondary angular sensing zone.

9. The base plate according to claim 1, wherein the base plate further comprises a tertiary angular sensing zone separate from the primary and secondary angular sensing zones and between the third direction and the first direction from the center point, the tertiary sensing zone having a third leakage electrode of the plurality of electrodes to enable detection of liquid between the third direction and the first direction.

10. The base plate according to claim 9, wherein the tertiary angular sensing zone spans a tertiary angle in the range from 45° to 180°.

11. The base plate according to claim 9, wherein the first leakage electrode comprises one or more tertiary first sensing parts arranged in the tertiary angular sensing zone.

12. The base plate according to claim 9, wherein the third leakage electrode comprises one or more tertiary third sensing parts arranged in the tertiary angular sensing zone.

13. A method of monitoring a base plate of an ostomy appliance, the base plate comprising an adhesive layer and a plurality of electrodes, the adhesive layer having a proximal side configured for attachment of the base plate to the skin surface of a user and a stomal opening with a center point, the plurality of electrodes including a first leakage electrode, a second leakage electrode, and a third leakage electrode, the method comprising:
   obtaining a primary sensor signal from the first leakage electrode and the second leakage electrode located in a primary angular sensing zone of the base plate between a first direction and a second direction from the center point;
   detecting presence of fluid on the proximal side in a primary angular sensing zone based on the primary sensor signal;
   obtaining a secondary sensor signal from the second leakage electrode and the third leakage electrode located in a secondary angular sensing zone separate from the primary angular sensing zone;
   detecting presence of fluid on the proximal side in a secondary angular sensing zone based on the secondary sensor signal; and
   in accordance with detection of presence of fluid in the primary angular sensing zone and/or the secondary angular sensing zone, providing a leakage indicator indicative of an angular sensing zone in which presence of liquid has been detected.

14. The base plate according to claim 1, wherein the first direction and the third direction are the same.

15. The method of claim 13, wherein the secondary angular sensing zone is between the second direction and a third direction from the center point.

16. The method of claim 15, wherein the first direction and the third direction are the same.

17. The method of claim 15, wherein the base plate further comprises a third angular sensing zone between the first direction and the third direction from the center point.

* * * * *